United States Patent [19]

Noguchi et al.

[11] Patent Number: 4,608,385

[45] Date of Patent: Aug. 26, 1986

[54] FUNGICIDAL N-PHENYLCARBAMATES

[75] Inventors: Hiroshi Noguchi, Toyonaka; Toshiro Kato, Takarazuka; Junya Takahashi, Nishinomiya; Yukio Ishiguri, Takarazuka; Shigeo Yamamoto, Ikeda; Katsuzo Kamoshita, Osaka, all of Japan

[73] Assignee: Sumitomo Chemical Company, Limited, Osaka, Japan

[21] Appl. No.: 436,073

[22] Filed: Oct. 22, 1982

[30] Foreign Application Priority Data

Oct. 29, 1981 [JP] Japan .................................. 56-174043
Jan. 19, 1982 [JP] Japan ...................................... 57-7257

[51] Int. Cl.$^4$ .................. C07C 155/02; C07C 155/08; A01N 47/10; A01N 43/08
[52] U.S. Cl. ...................................... 514/444; 560/29; 560/27; 514/476; 514/475; 514/449; 514/471; 514/472; 514/459; 514/450; 514/447; 514/445; 549/553; 549/511; 549/475; 549/510; 549/419; 549/346; 549/473; 549/60; 549/414; 549/69; 549/480; 558/393
[58] Field of Search ...................... 260/455 A, 465 D; 560/29, 27; 514/476, 475, 449, 471, 472, 459, 450, 444, 447, 445; 549/553, 511, 475, 510, 346, 473, 60, 414, 69, 480, 419

[56] References Cited

U.S. PATENT DOCUMENTS

| | | | |
|---|---|---|---|
| 3,933,470 | 1/1976 | Cross et al. | 260/455 A |
| 3,997,325 | 12/1976 | Cross et al. | 260/455 A |
| 4,086,246 | 4/1978 | Toth et al. | 260/455 A |
| 4,482,546 | 11/1984 | Takahashi et al. | 260/455 A |
| 4,501,756 | 2/1985 | Kato et al. | 260/455 A |

FOREIGN PATENT DOCUMENTS

| | | | |
|---|---|---|---|
| 2330242 | 6/1973 | Fed. Rep. of Germany | 260/455 A |
| 40-19103 | 8/1965 | Japan | 260/455 A |

OTHER PUBLICATIONS

"Chemical Abstracts" 88:100355e, Yoshimoto et al, 11/21/77.
Chem. Abs., Mukai, et al., 87:52961e.
Chemical Abstracts, 28, 2239.
Chemical Abstracts, 50, 5674e.
Chemical Abstracts, 55, 21021b.
Chemical Abstracts, 55, 13376f.
Collins et al, J. Chem. Soc., pp. 366-372, 1966.
Collins et al, J. Chem. Soc., pp. 61-63, 1968.

Primary Examiner—Henry R. Jiles
Assistant Examiner—Robert C. Whittenbaugh
Attorney, Agent, or Firm—Birch, Stewart, Kolasch & Birch

[57] ABSTRACT

Use of an N-phenylcarbamate of the formula:

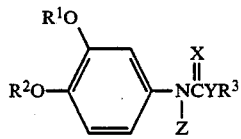

as a fungicidal agent against phytopathogenic fungi, particularly their strains resistant to benzimidazole thiophanate fungicides and/or cyclic imide fungicides.

42 Claims, No Drawings

FUNGICIDAL N-PHENYLCARBAMATES

This invention relates to fungicidal N-phenylcarbamates.

Benzimidazole thiophanate fungicides such as Benomyl (methyl 1-(butylcarbamoyl)benzimidazol-2-ylcarbamate), Fubelidazol (2-(2-furyl)benzimidazole), Thiabendazole (2-(4-thiazolyl)benzimidazole), Carbendazim (methyl benzimidazol-2-ylcarbamate), Thiophanate-methyl (1,2-bis(3-methoxycarbonyl-2-thioureido)benzene), Thiophanate (1,2-bis(3-ethoxycarbonyl-2-thioureido)benzene), 2-(O,S-dimethylphosphorylamino)-1-(3'-methoxycarbonyl-2'-thioureido)benzene and 2-(O,O-dimethylthiophosphorylamino)-1-(3'-methoxycarbonyl-2'-thioureido)benzene are known to show an excellent fungicidal activity against various plant pathogenic fungi, and they have been widely used as agricultural fungicides since 1970. However, their continuous application over a long period of time allows phytopathogenic fungi to develop a tolerance to them, whereby their plant disease-preventive effect is decreased. Further, the fungi which developed tolerance to certain kinds of benzimidazole thiophanate fungicides also show considerable tolerance to some other kinds of benzimidazole thiophanate fungicides. Thus, they are apt to develop cross-tolerance. Therefore, if any material decrease of their plant disease-preventive effect in certain fields is observed, their application to such fields has to be discontinued. But, it is often observed that the density of drug-resistant organisms is not decreased even long after the discontinuation of the application. Although other kinds of fungicides have to be employed in such a case, only few are so effective as benzimidazole thiophanate fungicides in controlling various phytopathogenic fungi. Cyclic imide fungicides such as Procymidone (3-(3',5'-dichlorophenyl)-1,2-dimethylcyclopropane-1,2-dicarboximide), Iprodione (3-(3',5'-dichlorophenyl)-1-isopropylcarbamoylimidazolidine-2,4-dione), Vinchlozoline (3-(3',5'-(dichlorophenyl)-5-methyl-5-vinyloxazolidin-2,4-dione), ethyl (RS)-3-(3',5'-dichlorophenyl)-5-methyl-2,4-dioxooxazolidine-5-carboxylate, etc., which are effective against various plant diseases, particularly those caused by *Botrytis cinerea*, have the same defects as previously explained with respect to the benzimidazole thiophanate fungicides.

In C.R. Acad. Sc. Paris, t. 289, S'erie, D, pages 691–693 (1979), it is described that such herbicides as Barban (4-chloro-2-butynyl N-(3-chlorophenyl)carbamate), Chlorobufam (1-methyl-2-propynyl N-(3-chlorophenyl)carbamate), Chloropropham (isopropyl N-(3-chlorophenyl)carbamate) and Propham (isopropyl N-phenylcarbamate) exhibit a fungicidal activity against certain organisms tolerant to some of benzimidazole thiophanate fungicides. However, their fungicidal activity against the drug-resistant fungi is not strong enough, and hence, practically they cannot be used as fungicides.

As a result of a study seeking a new type of fungicides, it has now been found that N-phenylcarbamates of the formula:

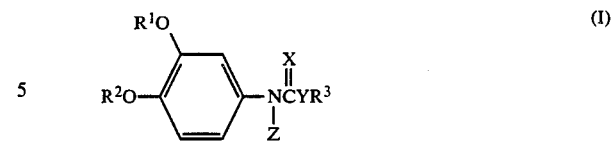

wherein $R^1$ and $R^2$ are, same or different, a lower alkyl group, a lower alkenyl group, a lower alkynyl group or a lower alkyl group substituted with at least one member selected from the group consisting of halogen, lower alkoxy and lower cycloalkyl; $R^3$ is a $C_1$–$C_8$ alkyl group, a $C_3$–$C_8$ alkenyl group, a $C_3$–$C_8$ alkynyl group, lower cycloalkyl group, a lower haloalkenyl group, a lower haloalkynyl group, a lower aralkyl group, a lower alkyl group substituted with at least one member selected from the group consisting of halogen, cyano, lower alkoxy, lower alkenyloxy, lower haloalkoxy, phenoxy, lower aralkyloxy and lower cycloalkyl, or a group of the formula:

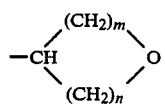

in which m is 0, 1 or 2, n is 1, 2 or 3; X and Y are, same or different, an oxygen atom or a sulfur atom; and Z is a hydrogen atom, a lower alkyl group, a lower alkenyl group, a lower alkynyl group, a lower cycloalkyl group, a lower haloalkenyl group, a lower alkyl group substituted with at least one member selected from the group consisting of halogen, cyano, lower alkoxy and lower alkoxycarbonyl, or a group of the formula: —$COR^4$ or —$SO_2R^4$ in which $R^4$ is a lower alkyl group, a lower alkenyl group, a lower alkynyl group, a lower cycloalkyl group, a lower haloalkenyl group, a lower alkyl group substituted with at least one member selected from the group consisting of halogen, cyano, lower alkoxy, lower cycloalkyl and phenoxy (phenoxy being optionally substituted with at least one halogen and/or at least one alkyl), a phenyl group, a furyl group, a thienyl group, a phenyl group substituted with at least one member selected from the group consisting of halogen, cyano, nitro, trifluoromethyl, lower alkyl and lower alkoxy, or an aralkyl group (aralkyl being optionally substituted with at least one halogen and/or at least one alkyl), with the proviso that when $R^1$ is methyl, $R^2$ is neither methyl nor butyl, show an excellent fungicidal activity against plant pathogenic fungi which have developed resistance to benzimidazole thiophanate fungicides and/or cyclic imide fungicides. It is notable that their fungicidal potency against the organisms tolerant to benzimidazole thiophanate fungicides and/or cyclic imide fungicides (hereinafter referred to as "drug-resistant fungi" or "drug-resistant strains") is much higher than that against the organisms sensitive to benzimidazole thiophanate fungicides and/or cyclic imide fungicides (hereinafter referred to as "drug-sensitive fungi" or "drug-sensitive strains").

The term "lower" used hereinabove and hereinafter in connection with organic radicals or compounds indicates that such radicals or compounds each have not more than 6 carbon atoms.

Some of N-(3,4-dialkoxyphenyl)carbamates have hitherto been synthesized, for instance, N-(3,4-dimethoxyphenyl)carbamates (C.A., 28, 2339; 50, 5674e), 2-chloroethyl N-(3-methoxy-4-octyloxyphenyl)carbamate (C.A., 55, 13376f; 55, 21021b), 2-chloroethyl N-(3-methoxy-4-butoxyphenyl)carbamate (C.A., 64, 8063g), ethyl N-(3-methoxy-4-octyloxyphenyl)carbamate (C.A., 68, 39300b) and so on are known. However, none of them shows any substantial fungicidal activity against drug-resistant fungi or is useful as a fungicide.

Thus, the present invention provides a fungicidal composition which comprises, as an active ingredient, a fungicidally effective amount of the N-phenylcarbamate (I) and an inert carrier or diluent. It also provides a combination composition comprising as active ingredients the N-phenylcarbamate (I) together with a benzimidazole thiophanate fungicide and/or a cyclic imide fungicide, which is fungicidally effective against not only drug-sensitive fungi but also drug-resistant fungi, and hence particularly effective for the prevention of plant diseases. It also provides a method of controlling plant pathogenic fungi including drug-resistant strains and drug-sensitive strains by applying a fungicidally effective amount of the N-phenylcarbamate (I) to plant pathogenic fungi. It further provides novel N-phenylcarbamates which are represented by the formula (I) wherein $R^1$, $R^2$, $R^3$, X, Y and Z are each as defined above with the proviso that when $R^1$ is methyl, $R^2$ is neither methyl or butyl. It furthermore provides a process for producing the novel N-phenylcarbamates (I).

The N-phenylcarbamates (I) can be prepared by various procedures, among which typical examples are shown below:

Procedure (a):

The N-phenylcarbamate (I) is obtainable by reacting a 3,4-dialkoxyaniline of the formula:

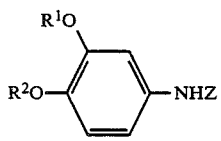
(II)

wherein $R^1$, $R^2$ and Z are each as defined above, with a chloroformate of the formula:

(III)

wherein $R^3$, X and Y are each as defined above.

The reaction is usually carried out in the presence of an inert solvent (e.g. benzene, toluene, xylene, diethyl ether, tetrahydrofuran, dioxane, chloroform, carbon tetrachloride, ethyl acetate, pyridine, dimethylformamide). When desired, the reaction may be performed in the existence of a dehydrohalogenating agent (e.g. pyridine, triethylamine, diethylaniline, sodium hydroxide, potassium hydroxide, sodium hydride) to obtain the objective compound (I) in a high yield. The reaction may be accomplished at a temperature of 0° to 150° C. instantaneously or within 12 hours.

Procedure (b):

The N-phenylcarbamate (I) wherein Z is hydrogen is obtainable by reacting a 3,4-dialkoxyphenyl isocyanate or isothiocyanate of the formula:

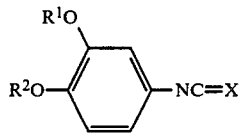
(IV)

wherein $R^1$, $R^2$ and X are each as defined above, with an alcohol or thiol of the formula:

$HYR^3$ (V)

wherein $R^3$ and Y are each as defined above.

The reaction is usually carried out in the absence or presence of an inert solvent (e.g. benzene, toluene, xylene, diethyl ether, tetrahydrofuran, dioxane, dimethylformamide, chloroform, carbon tetrachloride). When desired, a catalyst (e.g. triethylamine, diethylaniline, 1,4-diazabicyclo(2,2,2)octane) may be used. The reaction is normally accomplished at a temperature of 0° to 50° C. instantaneously or within 12 hours.

Procedure (c):

The N-phenylcarbamate (I) wherein Z is not hydrogen is obtainable by reacting an N-(3,4-dialkoxyphenyl)carbamate of the formula:

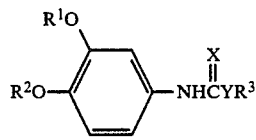
(VI)

wherein $R^1$, $R^2$, $R^3$, X and Y are each as defined above, with a halide of the formula:

A—Z (VII)

wherein Z is as defined above except hydrogen and A is a halogen atom (e.g. chlorine, bromine).

The reaction is usually carried out in an inert solvent (e.g. benzene, toluene, xylene, diethyl ether, tetrahydrofuran, dioxane, chloroform, carbon tetrachloride, ethyl acetate, pyridine, dimethylformamide). When desired, the reaction may be performed in the existence of a dehydrohalogenating agent (e.g. pyridine, triethylamine, diethylaniline, sodium hydroxide, potassium hydroxide, sodium hydride) and a catalyst (e.g. tetrabutylammonium bromide) to obtain the objective compound (I) in a high yield. The reaction may be accomplished at a temperature of 0° to 150° C. instantaneously or within 12 hours.

As specific examples of the symbols used in the above formula, $R^1$ and $R^2$ are each preferably methyl, ethyl, n-propyl, isopropyl, n-butyl, allyl, 2-butenyl, 3-butenyl, propargyl, 3-butynyl, difluoromethyl, 2-chloroethyl, 2,2,2-trifluoromethyl, 2-methoxyethyl or cyclopropylmethyl, $R^3$ is methyl, ethyl, n-propyl, isopropyl, sec-butyl, 1-ethylpropyl, 1-methylbutyl, 1-ethylbutyl, 1,3-dimethylbutyl, 1-methylheptyl, allyl, 1-methyl-2-propenyl, 2-butenyl, 3-butenyl, 2-methyl-2-propenyl, 1-ethyl-2-propenyl, 1-methyl-3-butenyl, 1-pentyl-2-propenyl, propargyl, 1-methyl-2-propynyl, 2-butynyl, 3-butynyl, 1-ethyl-2-propynyl, 1-methyl-3-butynyl, 1-butyl-2-propynyl, 1-pentyl-2-propynyl, cyclobutyl, cyclopentyl, 2-fluoroethyl, 2-chloroethyl, 2,2-dichloroethyl, 1-methyl-2-bromoethyl, 1-fluoromethyl-2-fluoroethyl, 1-bromomethyl-2-bromoethyl, 1-methyl-2,2,2-trichloroethyl, 1-ethyl-2-bromoethyl, 4-chloro-2-butenyl, 4-chloro-2-butynyl, 2-cyanoethyl, 1-methyl-2-methoxyethyl, 1-methyl-2-butoxyethyl, 2-allyloxyethyl, 2-(2-chloroethoxy)ethyl, 2-benzyloxyethyl, 1-chloromethyl-2-methoxyethyl, cyclopropylmethyl, 1-cyclopropylethyl, 1-cyclopentylethyl, 3-furylmethyl, 1-phenylethyl or 3-tetrahydrofuranyl, X and Y are each oxygen or sulfur, and Z is hydrogen, methyl, ethyl, n-butyl, allyl, acetyl, propionyl, n-pentanoyl, sec-pentanoyl, cyclopropanecarbonyl, benzoyl, 2-chlorobenzoyl, 2,4-dichlorobenzoyl, 4-methylbenzoyl, methanesulfonyl or ethoxycarbonylmethyl.

The N-phenylcarbamates (I) are fungicidally effective against a wide scope of plant pathogenic fungi, of which examples are as follows: Podosphaera leucotricha, Venturia inaegualis, Mycosphaerella pomi, Marssonina mali and Sclerotinia mali of apple, Phyllactinia kakicola and Gloeosporium kaki of persimmon, Cladosporium carpophilum and Phomopsis sp. of peach, Cercospora, viticola, Uncinula necator, Elsinoe ampelina and Glomerella cingulata of grape, Cercospora beticola of sugarbeet, Cercospora arachidicola and Cercospora personata of peanut, Erysiphe graminis f. sp. hordei, Cercosporella herpotrichoides and Fusarium nivale of barley, Erysiphe graminis f. sp. tritici of wheat, Sphaerotheca fuliginea and Cladosporium cucumerinum of cucumber, Cladosporium fulvum of tomato, Corynespora melongenae of eggplant, Sphaerotheca humuli, Fusarium oxysporum f. sp. fragariae of strawberry, Botrytis alli of onion, cercospora apii of cerely, Phaeoisariopsis griseola of kidney bean, Erysiphe cichoracearum of tabacco, Diplocarpon rosae of rose, Elsinoe fawcetti, Penicillium italicum, Penicillium digitatum of orange, Botrytis cinerea of cucumber, eggplant, tomato, strawberry, pimiento, onion, lettuce, grape, orange, cyclamen, rose or hop, Sclerotinia sclerotiorum of cucumber, eggplant, pimiento, lettuce, celery, kidney bean, soybean, azuki bean, potato or sunflower, Sclerotinia cinerea of peach or cherry, Mycosphaerella melonis of cucumber or melon, etc. Namely, the N-phenylcarbamates (I) are highly effective in controlling the drug-resistant strains of the fungi.

The N-phenylcarbamates (I) are also fungicidally effective against fungi sensitive to known fungicides as well as fungi to which known fungicides are ineffective. Examples of such fungi are Pyricularia oryzae, Pseudoperonospora cubensis, Plasmopara viticola, Phytophthora infestans, etc.

Advantageously, the N-phenylcarbamates (I) are low in toxicity and have little detrimental effects on mammals, fishes and so on. Also, they may be applied to the agricultural field without causing any material toxicity to important crop plants.

In view of their excellent fungicidal properties, preferred are the compounds of the formula (I) wherein $R^1$ and $R^2$ are independently methyl, ethyl, n-propyl, isopropyl, n-butyl, allyl, 2-butenyl, 3-butenyl, propargyl, 3-butynyl, difluoromethyl, 2-chloroethyl, 2,2,2-trifluoroethyl, 2-methoxyethyl or cyclopropylmethyl, $R^3$ is methyl, ethyl, n-propyl, isopropyl, sec-butyl, 1-ethylpropyl, 1-methylbutyl, 1-ethylbutyl, 1,3-dimethylbutyl, 1-methylheptyl, allyl, 1-methyl-2-propenyl, 2-butenyl, 3-butenyl, 2-methyl-2-propenyl, 1-ethyl-2-propenyl, 1-methyl-3-butenyl, 1-pentyl-2-propenyl, propargyl, 1-methyl-2-propynyl, 2-butynyl, 3-butynyl, 1-ethyl-2-propynyl, 1-methyl-3-butynyl, 1-butyl-2-propynyl, 1-pentyl-2-propynyl, cyclobutyl, cyclopentyl, 2-fluoroethyl, 2-chloroethyl, 2,2-dichloroethyl, 1-methyl-2-bromoethyl, 1-fluoromethyl-2-fluoroethyl, 1-bromomethyl-2-bromoethyl, 1-methyl-2,2,2-trichloroethyl, 1-ethyl-2-bromoethyl, 4-chloro-2-butenyl, 4-chloro-2-butynyl, 2-cyanoethyl, 1-methyl-2-methoxyethyl, 1-methyl-2-butoxyethyl, 2-allyloxyethyl, 2-(2-chloroethoxy)ethyl, 2-benzyloxyethyl, 1-chloromethyl-2-methoxyethyl, cyclopropylmethyl, 1-cyclopropylethyl, 1-cyclopentylethyl, 2-furylmethyl, 1-phenylethyl or 3-tetrahydrofuranyl, X and Y are independently oxygen or sulfur, and Z is hydrogen, methyl, ethyl, n-butyl, allyl, acetyl, propionyl, n-pentanoyl, sec-pentanoyl, cyclopropanecarbonyl, benzoyl, 2-chlorobenzoyl, 2,4-dichlorobenzoyl, 4-methylbenzoyl, methanesulfonyl or ethoxycarbonylmethyl, with the proviso that when $R^1$ is methyl, $R^2$ is neither methyl or butyl.

Particularly preferred are the compounds of the formula (I) wherein $R^1$ and $R^2$ are independently methyl, ethyl, n-propyl, allyl or propargyl, $R^3$ is ethyl, isopropyl, sec-butyl, 1-methylbutyl, 1-ethylpropyl, 1-ethylbutyl, 1-methyl-2-propenyl, 1-ethyl-2-propenyl, 1-methyl-3-butenyl, propargyl, 1-methyl-2-propynyl, 1-ethyl-2-propynyl, 3-butynyl, 1-methyl-3-butynyl, 1-butyl-2-propynyl, 2-fluoroethyl, 1-methyl-2-bromoethyl, 1-fluoromethyl-2-fluoroethyl, 1-bromomethyl-2-bromoethyl, 4-chloro-2-butynyl, 1-methyl-2-methoxyethyl, 1-cyclopropylethyl or 1-phenylethyl, X is oxygen, Y is oxygen or sulfur, and Z is hydrogen, acetyl, propionyl, n-pentanoyl, sec-pentanoyl, cyclopropanecarbonyl, benzoyl, 2-chlorobenzoyl, 2,4-dichlorobenzoyl or 4-methylbenzoyl, with the proviso that when $R^1$ is methyl, $R^2$ is not methyl.

More preferred are the compound of the formula (I) wherein $R^1$ and $R^2$ are each ethyl, $R^3$ is ethyl, isopropyl, sec-butyl, 1-methylbutyl, 1-ethylbutyl, 1-methyl-3-butenyl, 1-methyl-2-propynyl, 4-chloro-2-butynyl or 1-phenylethyl, X is oxygen, Y is oxygen or sulfur and Z is hydrogen, acetyl, cyclopropanecarbonyl, benzoyl or 2-chlorobenzoyl.

Most preferred are the following:

Isopropyl N-(3,4-diethoxyphenyl)carbamate;
1-Methyl-2-propynyl N-(3,4-diethoxyphenyl)carbamate;
4-Chloro-2-butynyl N-(3,4-diethoxyphenyl)carbamate;
Isopropyl N-(3,4-diethoxyphenyl)thiolcarbamate;
1-Phenylethyl N-(3,4-diethoxyphenyl)carbamate;
Isopropyl N-acetyl-N-(3,4-diethoxyphenyl)carbamate;
Isopropyl N-cyclopropanecarbonyl-N-(3,4-diethoxyphenyl)carbamate;
Isopropyl N-benzony-N-(3,4-diethoxyphenyl)carbamate;
Isopropyl N-(2-chlorobenzoyl)-N-(3,4-diethoxyphenyl)carbamate, etc.

Some typical examples of the procedures for preparation of the N-phenylcarbamates (I) are illustratively shown in the following examples.

EXAMPLE 1

Preparation of isopropyl N-(3,4-diethoxyphenyl)carbamate according to Procedure (a)

3,4-Diethoxyaniline (1.8 g) and diethylaniline (1.5 g) were dissolved in benzene (20 ml). To the resultant solution was dropwise added isopropyl chloroformate (1.2 g) in 5 minutes under ice-cooling. After being allowed to stand at room temperatue for 3 hours, the reaction mixture was poured into ice-water and extracted with ether. The extract was washed with water, dried over magnesium sulfate and concentrated under reduced pressure to give crude crystals (2.6 g). Recrystallization from ethanol gave isopropyl N-(3,4-diethoxyphenyl)carbamate (Compound No. 13) (2.3 g) in a yield of 86%. M.P., 100°–100.5° C.

Elementary analysis: Calcd. for $C_{14}H_{21}NO_4$: C, 62.90%; H, 7.92%; N, 5.24%. Found: C, 62.75; H, 7.96%; N, 5.41%.

EXAMPLE 2

Preparation of isopropyl N-(3,4-diethoxyphenyl)thiolcarbamate according to Procedure (b)

Triethylamine (1 g) and isopropyl mercaptan (0.8 g) were dissolved in toluene (20 ml). To the resultant solution was dropwise added 3,4-diethoxyphenyl isocyanate (2.1 g) in 5 minutes under ice-cooling. After being allowed to stand at room temperature for 12 hours, the reaction mixture was poured into ice-water and extracted with toluene. The extract was washed with water, dried over magnesium sulfate and concentrated under reduced pressure. The residue was purified by silica gel chromatography using toluene as the eluent to give isopropyl N-(3,4-diethoxyphenyl)thiolcarbamate (Compound No. 88) (2.7 g) in a yield of 95%. M.P., 110°–111° C.

Elementary analysis: Calcd. for $C_{14}H_{21}NO_3S$: C, 59.33%; H, 7.47%; N, 4.94%; S, 11.32%. Found: C, 59.02%; H, 7.51%; N, 4.89%; S, 11.70%.

EXAMPLE 3

Preparation of isopropyl N-benzoyl-N-(3,4-diethoxyphenyl)carbamate according to Procedure (c)

Isopropyl N-(3,4-diethoxyphenyl)carbamate (2.7 g) was dissolved in dimethylformamide (50 ml), and sodium hydride dispersion (50%, 0.5 g) was added thereto. The mixture was heated at 60° C. for 15 minutes, treated with benzoyl chloride (1.4 g) and heated for 30 minutes. The reaction mixture was poured into ice-water and extracted with ether. The extract was washed with sodium bicarbonate solution and saturated brine, dried over anhydrous magnesium sulfate and concentrated under reduced pressure. The residue was purified by silica gel chromatography using hexane-acetone as the eluent to give isopropyl N-benzoyl-N-(3,4-diethoxyphenyl)carbamate (Compound No. 99) (3.1 g) in a yield of 80%. M.P., 120°–121° C.

Elementary analysis: Calcd. for $C_{21}H_{25}NO_5$: C, 67.90%; H, 6.78%; N, 3.77%. Found: C, 68.11%; H, 6.61%; N, 3.90%.

According to either one of the above Procedures (a), (b) or (c), the N-phenylcarbamates of the formula (I) as shown in Table 1 can be prepared:

TABLE 1

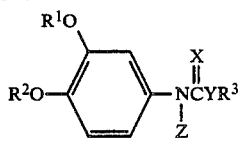

| Compound No. | $R^1$ | $R^2$ | $R^3$ | X | Y | Z | Physical constant |
|---|---|---|---|---|---|---|---|
| 1 | —CH$_3$ | —C$_2$H$_5$ | —C$_3$H$_7$(iso) | O | O | H | M.P. 104–105° C. |
| 2 | —CH$_3$ | —C$_2$H$_5$ | —CHCH$_3$(C≡CH) | O | O | H | M.P. 133–134° C. |
| 3 | —CH$_3$ | —C$_2$H$_5$ | —CHCH$_2$OCH$_3$(CH$_3$) | O | O | H | M.P. 54–55° C. |
| 4 | —CH$_3$ | —C$_3$H$_7$(n) | —C$_3$H$_7$(iso) | O | O | H | M.P. 94–95° C. |
| 5 | —CH$_3$ | —CH$_2$CH=CH$_2$ | —C$_3$H$_7$(iso) | O | O | H | M.P. 79–80° C. |
| 6 | —CH$_3$ | —CH$_2$CH=CH$_2$ | —CHCH$_3$(C≡CH) | O | O | H | M.P. 106–107° C. |
| 7 | —CH$_3$ | —CH$_2$C≡CH | —C$_3$H$_7$(iso) | O | O | H | $n_D^{19}$ 1.5269 |
| 8 | —C$_2$H$_5$ | —CH$_3$ | —C$_3$H$_7$(iso) | O | O | H | M.P. 103–104° C. |
| 9 | —C$_2$H$_5$ | —CH$_3$ | —CHCH$_2$CH$_3$(C≡CH) | O | O | H | M.P. 110.5–111.5° C. |
| 10 | —C$_2$H$_5$ | —CH$_3$ | —CH$_2$C≡CCH$_2$Cl | O | O | H | M.P. 96–97° C. |
| 11 | —C$_2$H$_5$ | —C$_2$H$_5$ | —CH$_3$ | O | O | H | M.P. 120–121° C. |
| 12 | —C$_2$H$_5$ | —C$_2$H$_5$ | —C$_2$H$_5$ | O | O | H | M.P. 90–91° C. |
| 13 | —C$_2$H$_5$ | —C$_2$H$_5$ | —C$_3$H$_7$(iso) | O | O | H | M.P. 100–100.5° C. |
| 14 | —C$_2$H$_5$ | —C$_2$H$_5$ | —C$_4$H$_9$(sec) | O | O | H | M.P. 97–98° C. |
| 15 | —C$_2$H$_5$ | —C$_2$H$_5$ | —CH(CH$_2$)$_2$CH$_3$(CH$_3$) | O | O | H | M.P. 67–68° C. |

TABLE 1-continued

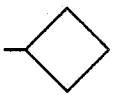

| Compound No. | R¹ | R² | R³ | X | Y | Z | Physical constant |
|---|---|---|---|---|---|---|---|
| 16 | $-C_2H_5$ | $-C_2H_5$ | $-\underset{\underset{CH_2CH_3}{\|}}{CH}CH_2CH_3$ | O | O | H | M.P. 93–94° C. |
| 17 | $-C_2H_5$ | $-C_2H_5$ | $-\underset{\underset{CH(CH_2)_2CH_3}{\|}}{CH}CH_2CH_3$ | O | O | H | M.P. 87–88° C. |
| 18 | $-C_2H_5$ | $-C_2H_5$ | $-CH(CH_3)CH_2CH(CH_3)$ | O | O | H | M.P. 56–57° C. |
| 19 | $-C_2H_5$ | $-C_2H_5$ | $-CH(CH_3)(CH_2)_5CH_3$ | O | O | H | M.P. 46.5–48° C. |
| 20 | $-C_2H_5$ | $-C_2H_5$ | $-CH_2CH=CH_2$ | O | O | H | M.P. 86–87° C. |
| 21 | $-C_2H_5$ | $-C_2H_5$ | $-CH(CH_3)CH=CH_2$ | O | O | H | M.P. 98–99.5° C. |
| 22 | $-C_2H_5$ | $-C_2H_5$ | $-CH_2CH_2CH=CH_2$ | O | O | H | M.P. 92.5–93.5° C. |
| 23 | $-C_2H_5$ | $-C_2H_5$ | $-CH_2C(CH_3)=CH_2$ | O | O | H | M.P. 92–93° C. |
| 24 | $-C_2H_5$ | $-C_2H_5$ | $-CH(CH_2CH_3)CH=CH_2$ | O | O | H | M.P. 98.5–99.5° C. |
| 25 | $-C_2H_5$ | $-C_2H_5$ | $-CH(CH_3)CH_2CH=CH_2$ | O | O | H | M.P. 75–76° C. |
| 26 | $-C_2H_5$ | $-C_2H_5$ | $-CH(CH=CH_2)(CH_2)_4CH_3$ | O | O | H | M.P. 46.5–48° C. |
| 27 | $-C_2H_5$ | $-C_2H_5$ | $-CH_2C\equiv CH$ | O | O | H | M.P. 111–112° C. |
| 28 | $-C_2H_5$ | $-C_2H_5$ | $-CH(CH_3)C\equiv CH$ | O | O | H | M.P. 116–117° C. |
| 29 | $-C_2H_5$ | $-C_2H_5$ | $-CH_2CH_2C\equiv CH$ | O | O | H | M.P. 89–90° C. |
| 30 | $-C_2H_5$ | $-C_2H_5$ | $-CH(CH_2CH_3)C\equiv CH$ | O | O | H | M.P. 118–119° C. |
| 31 | $-C_2H_5$ | $-C_2H_5$ | $-CH(CH_3)CH_2C\equiv CH$ | O | O | H | M.P. 99–100° C. |
| 32 | $-C_2H_5$ | $-C_2H_5$ | $-CH(C\equiv CH)(CH_2)_3CH_3$ | O | O | H | M.P. 120–121° C. |
| 33 | $-C_2H_5$ | $-C_2H_5$ | $-CH(C\equiv CH)(CH_2)_4CH_3$ | O | O | H | M.P. 96–97° C. |
| 34 | $-C_2H_5$ | $-C_2H_5$ | cyclobutyl | O | O | H | M.P. 114–115.5° C. |
| 35 | $-C_2H_5$ | $-C_2H_5$ | $-CH_2CH_2F$ | O | O | H | M.P. 101–102° C. |

TABLE 1-continued

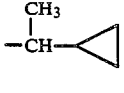

| Compound No. | R¹ | R² | R³ | X | Y | Z | Physical constant |
|---|---|---|---|---|---|---|---|
| 36 | $-C_2H_5$ | $-C_2H_5$ | $-CH_2CH_2Cl$ | O | O | H | M.P. 89.5-90.5° C. |
| 37 | $-C_2H_5$ | $-C_2H_5$ | $-CH_2CHCl_2$ | O | O | H | M.P. 73-74° C. |
| 38 | $-C_2H_5$ | $-C_2H_5$ | $-CH(CH_3)CH_2Br$ | O | O | H | M.P. 69-70° C. |
| 39 | $-C_2H_5$ | $-C_2H_5$ | $-CH(CH_2F)CH_2F$ | O | O | H | M.P. 89-90° C. |
| 40 | $-C_2H_5$ | $-C_2H_5$ | $-CH(CH_2Br)CH_2Br$ | O | O | H | M.P. 75-76° C. |
| 41 | $-C_2H_5$ | $-C_2H_5$ | $-CH(CH_3)CCl_3$ | O | O | H | $n_D^{19.5}$ 1.5316 |
| 42 | $-C_2H_5$ | $-C_2H_5$ | $-CH_2CH=CHCH_2Cl$ | O | O | H | M.P. 82-83° C. |
| 43 | $-C_2H_5$ | $-C_2H_5$ | $-CH_2C\equiv CCH_2Cl$ | O | O | H | M.P. 112-113° C. |
| 44 | $-C_2H_5$ | $-C_2H_5$ | $-CH_2CH_2OCH_2CH=CH_2$ | O | O | H | M.P. 58-59° C. |
| 45 | $-C_2H_5$ | $-C_2H_5$ | $-CH_2CH_2OCH_2CH_2Cl$ | O | O | H | M.P. 77-78° C. |
| 46 | $-C_2H_5$ | $-C_2H_5$ | $-CH(CH_3)CH_2OCH_3$ | O | O | H | M.P. 65-66.5° C. |
| 47 | $-C_2H_5$ | $-C_2H_5$ | $-CH(CH_3)CH_2O(CH_2)_3CH_3$ | O | O | H | M.P. 36-38° C. |
| 48 | $-C_2H_5$ | $-C_2H_5$ | $-CH(CH_2Cl)CH_2OCH_3$ | O | O | H | M.P. 82-83° C. |
| 49 | $-C_2H_5$ | $-C_2H_5$ | $-CH_2CH_2CN$ | O | O | H | M.P. 85.5-86.5° C. |
| 50 | $-C_2H_5$ | $-C_2H_5$ | $-CH(CH_3)$-cyclopropyl | O | O | H | M.P. 107-108° C. |
| 51 | $-C_2H_5$ | $-C_3H_7(n)$ | $-C_2H_5$ | O | O | H | M.P. 74-75° C. |
| 52 | $-C_2H_5$ | $-C_3H_7(n)$ | $-C_3H_7(iso)$ | O | O | H | M.P. 97-98° C. |
| 53 | $-C_2H_5$ | $-C_2H_5$ | $-CH(CH_3)C\equiv CH$ | O | O | H | M.P. 99-100° C. |
| 54 | $-C_2H_5$ | $-C_4H_9(n)$ | $-C_3H_7(iso)$ | O | O | H | M.P. 110-111° C. |
| 55 | $-C_2H_5$ | $-C_4H_9(n)$ | $-CH(CH_3)CH_2OCH_3$ | O | O | H | M.P. 87-88° C. |
| 56 | $-C_2H_5$ | $-CH_2C\equiv CH$ | $-C_3H_7(iso)$ | O | O | H | M.P. 102-103° C. |
| 57 | $-C_3H_7(n)$ | $-CH_3$ | $-C_3H_7(iso)$ | O | O | H | M.P. 101-102° C. |
| 58 | $-C_3H_7(n)$ | $-C_2H_5$ | $-CH_3$ | O | O | H | M.P. 85-86° C. |
| 59 | $-C_3H_7(n)$ | $-C_2H_5$ | $-C_2H_5$ | O | O | H | M.P. 76.5-77.5° C. |
| 60 | $-C_3H_7(n)$ | $-C_2H_5$ | $-C_3H_7(iso)$ | O | O | H | M.P. 81-82° C. |
| 61 | $-C_3H_7(n)$ | $-C_2H_5$ | $-CH(CH_3)CH_2CH_2$ | O | O | H | M.P. 83-84° C. |
| 62 | $-C_3H_7(n)$ | $-C_2H_5$ | $-CH(CH_2CH_3)CH_2CH_3$ | O | O | H | M.P. 90-91° C. |

TABLE 1-continued $$\underset{R^2O}{\overset{R^1O}{\phantom{...}}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\phantom{.}\text{–}\!\!\underset{Z}{\overset{X}{\underset{|}{\overset{\|}{N}}\!\!\text{CYR}^3}}$$

| Compound No. | R¹ | R² | R³ | X | Y | Z | Physical constant |
|---|---|---|---|---|---|---|---|
| 63 | —C₃H₇(n) | —C₂H₅ | —CH(CH₃)-cyclopropyl | O | O | H | M.P. 82–83° C. |
| 64 | —C₃H₇(n) | —C₂H₅ | —CH₂CH₂F | O | O | H | M.P. 82–83° C. |
| 65 | —C₃H₇(n) | —C₃H₇(n) | —C₃H₇(iso) | O | O | H | M.P. 85–86° C. |
| 66 | —C₃H₇(iso) | —C₂H₅ | —C₃H₇(iso) | O | O | H | $n_D^{19}$ 1.5121 |
| 67 | —C₃H₇(iso) | —C₂H₅ | —CH(CH₃)C≡CH | O | O | H | M.P. 100.5–102° C. |
| 68 | —C₃H₇(iso) | —C₂H₅ | —CH(CH₃)CH₂OCH₃ | O | O | H | $n_D^{19}$ 1.5092 |
| 69 | —C₄H₉(n) | —C₂H₅ | —C₃H₇(iso) | O | O | H | M.P. 79.5–81° C. |
| 70 | —CH₂CH=CH₂ | —C₃H₇(n) | —C₃H₇(iso) | O | O | H | M.P. 82–83° C. |
| 71 | —CH₂CH=CH₂ | —C₃H₇(n) | —CH₂CH=CHCH₃ | O | O | H | M.P. 66–67° C. |
| 72 | —CH₂CH=CH₂ | —C₃H₇(n) | —CH₂C≡CCH₃ | O | O | H | M.P. 92–93° C. |
| 73 | —CH₂CH=CH₂ | —C₃H₇(n) | —CH(CH₃)C≡CH | O | O | H | M.P. 84–85.5° C. |
| 74 | —CH₂CH=CH₂ | —CH₂CH=CH₂ | —C₃H₇(iso) | O | O | H | M.P. 83.5–84.5° C. |
| 75 | —CH₂C=CH₂ | —C₂H₅ | —C₃H₇(iso) | O | O | H | M.P. 101–102° C. |
| 76 | —CH₂C=CH₂ | —CH₂C≡CH | —C₃H₇(iso) | O | O | H | M.P. 103–104° C. |
| 77 | —CHF₂ | —CHF₂ | —C₃H₇(iso) | O | O | H | $n_D^{22}$ 1.4671 |
| 78 | —C₂H₅ | —C₂H₅ | —CH₂CH₂OCH₂-phenyl | O | O | H | M.P. 73–74° C. |
| 79 | —C₂H₅ | —C₂H₅ | —CH₂-cyclopropyl | O | O | H | M.P. 95–96° C. |
| 80 | —C₂H₅ | —C₂H₅ | —CH(CH₃)-cyclopentyl | O | O | H | M.P. 105–106° C. |
| 81 | —C₂H₅ | —C₂H₅ | —CH(CH₂CH₃)CH₂Br | O | O | H | M.P. 68–69° C. |
| 82 | —CH₂CH₂Cl | —C₂H₅ | —C₃H₇(iso) | O | O | H | M.P. 111–112° C. |
| 83 | —C₂H₅ | —C₂H₅ | —C₃H₇(n) | O | O | H | M.P. 79–80° C. |
| 84 | —C₂H₅ | —C₂H₅ | tetrahydrofuran-yl | O | O | H | M.P. 117–118° C. |
| 85 | —C₂H₅ | —C₂H₅ | —CH₂-furyl | O | O | H | M.P. 111.5–112.5° C. |
| 86 | —C₂H₅ | —C₂H₅ | —CH(CH₃)-phenyl | O | O | H | M.P. 109–110° C. |
| 87 | —C₂H₅ | —C₂H₅ | —C₂H₅ | O | S | H | M.P. 107–108° C. |

TABLE 1-continued $$R^2O\underset{R^1O}{\overset{}{\bigcirc}}-\underset{Z}{\overset{X}{N-CYR^3}}$$

| Compound No. | $R^1$ | $R^2$ | $R^3$ | X | Y | Z | Physical constant |
|---|---|---|---|---|---|---|---|
| 88 | —$C_2H_5$ | —$C_2H_5$ | —$C_3H_7$(iso) | O | S | H | M.P. 110–111° C. |
| 89 | —$C_2H_5$ | —$C_2H_5$ | —$CH_2CH=CH_2$ | O | S | H | M.P. 73–76° C. |
| 90 | —$C_2H_5$ | —$C_2H_5$ | —$C_2H_5$ | O | O | —$CH_3$ | $n_D^{28.5}$ 1.5059 |
| 91 | —$C_2H_5$ | —$C_2H_5$ | —$C_3H_7$(iso) | O | O | —$C_2H_5$ | $n_D^{28.5}$ 1.4922 |
| 92 | —$C_2H_5$ | —$C_2H_5$ | —$C_3H_7$(iso) | O | O | —$C_4H_9$(n) | $n_D^{26.5}$ 1.4885 |
| 93 | —$C_2H_5$ | —$C_2H_5$ | —$C_3H_7$(iso) | O | O | —$CH_2CH=CH_2$ | $n_D^{26.5}$ 1.5044 |
| 94 | —$C_2H_5$ | —$C_2H_5$ | —$C_3H_7$(iso) | O | O | —$COCH_3$ | M.P. 98–99° C. |
| 95 | —$C_2H_5$ | —$C_2H_5$ | —$C_3H_7$(iso) | O | O | —$COC_2H_5$ | $n_D^{27.5}$ 1.5006 |
| 96 | —$C_2H_5$ | —$C_2H_5$ | —$C_3H_7$(iso) | O | O | —$COC_4H_9$(n) | M.P. 63–65° C. |
| 97 | —$C_2H_5$ | —$C_2H_5$ | —$C_3H_7$(iso) | O | O | —$COC_4H_9$(sec) | $n_D^{28}$ 1.4889 |
| 98 | —$C_2H_5$ | —$C_2H_5$ | —$C_3H_7$(iso) | O | O | —CO-cyclopropyl | M.P. 55–57° C. |
| 99 | —$C_2H_5$ | —$C_2H_5$ | —$C_3H_7$(iso) | O | O | —CO-phenyl | M.P. 120–121° C. |
| 100 | —$C_2H_5$ | —$C_2H_5$ | —$C_3H_7$(iso) | O | O | —CO-(2-Cl-phenyl) | $n_D^{28}$ 1.5371 |
| 101 | —$C_2H_5$ | —$C_2H_5$ | —$C_3H_7$(iso) | O | O | —CO-(2,4-diCl-phenyl) | $n_D^{28.5}$ 1.5349 |
| 102 | —$C_2H_5$ | —$C_2H_5$ | —$C_3H_7$(iso) | O | O | —CO-(4-$CH_3$-phenyl) | M.P. 102–103° C. |
| 103 | —$C_2H_5$ | —$C_2H_5$ | $\underset{-CHCH_2OCH_3}{CH_3}$ | O | O | —$COC_2H_5$ | $n_D^{27}$ 1.4972 |
| 104 | —$C_2H_5$ | —$C_2H_5$ | —$C_3H_7$(iso) | O | O | —$SOCH_3$ | M.P. 114–115° C. |
| 105 | —$C_2H_5$ | —$C_2H_5$ | —$C_3H_7$(iso) | O | O | —$CH_2COOC_2H_5$ | $n_D^{27.5}$ 1.4948 |
| 106 | —$C_2H_5$ | —$C_2H_5$ | —$C_2H_5$ | S | O | H | M.P. 74–75° C. |
| 107 | —$C_2H_5$ | —$C_2H_5$ | —$CH_3$ | S | O | H | M.P. 87–88° C. |
| 108 | —$C_2H_5$ | —$C_2H_5$ | —$C_4H_9$(sec) | O | S | H | M.P. 97–98° C. |
| 109 | —$C_2H_5$ | —$C_2H_5$ | —$C_3H_7$(iso) | S | S | H | M.P. 64–65° C. |

In the practical use of the N-phenylcarbamates (I) as fungicides, they may be applied as such or in a preparation form such as dusts, wettable powders, oil sprays, emulsifiable concentrates, tablets, granules, fine granules, aerosols or flowables. Such a preparation form can be prepared in a conventional manner by mixing at least one of the N-phenylcarbamates (I) with an appropriate solid or liquid carrier(s) or diluent(s) and, if necessary, an appropriate adjuvant(s) (e.g. surfactants, adherents, dispersants, stabilizers) for improving the dispersibility and other properties of the active ingredient(s).

Examples of the solid carriers or diluents are botanical materials (e.g. flour, tobacco stalk powder, soybean powder, walnut-shell powder, vegetable powder, saw dust, bran, bark powder, cellulose powder, vegetable extract residue), fibrous materials (e.g. paper, corrugated cardboard, old rags), synthetic plastic powders, clays (e.g. kaolin, bentonite, fuller's earth), talcs, other inorganic materials (e.g. pyrophyllite, sericite, pumice, sulfur powder, active carbon) and chemical fertilizers (e.g. ammonium sulfate, ammonium phosphate, ammonium nitrate, urea, ammonium chloride).

Examples of the liquid carriers or diluents are water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methyl naphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, carbon tetrachloride), etc.

Examples of the surfactants are alkyl sulfuric esters, alkyl sulfonates, alkylaryl sulfonates, polyethylene glycol ethers, polyhydric alcohol esters, etc. Examples of the adherents and dispersants may include cesein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphate mixture), TCP (tricresyl phosphate), tolu oil, epoxydized oil, various surfactants, verious fatty acids and their esters, etc.

The foregoing preparations generally contain at least one of the N-phenylcarbamates (I) in a concentration of about 1 to 95% by weight, preferably of 2.0 to 80% by weight. By using the preparations, the N-phenylcarbamates (I) are generally applied in such amounts as 2 to 100 g per 10 are.

When only the drug-resistant strains of phytopathogenic fungi are present, the N-phenylcarbamates (I) may be used alone. However, when the drug-sensitive strains are present together with the drug-resistant strains, their alternate use with benzimidazole thiophanate fungicides and/or cyclic imide fungicides or their combined use with benzimidazole thiophanate fungicides and/or cyclic imide fungicides is favorable. In such alternate or combined use, each active ingredient may be employed as such or in conventional agricultural preparation forms. In case of the combined use, the weight proportion of the N-phenylcarbamate (I) and the benzimidazole thiophanate fungicide and/or the cyclic imide fungicide may be from about 1:0.1 to 1:10.0.

Typical examples of the benzimidazole thiophanate fungicides and the cyclic imide fungicides are shown in Table 2.

TABLE 2

| Compound | Structure | Name |
|---|---|---|
| A | benzimidazole with -NHCOOCH$_3$ at 2-position and -CONHC$_4$H$_9$(n) at N1 | Methyl 1-(butylcarbamoyl)benzimidazol-2-ylcarbamate |
| B | 2-(4-thiazolyl)benzimidazole structure | 2-(4-Thiazolyl)benzimidazole |
| C | benzimidazole with -NHCOOCH$_3$ at 2-position | Methyl benzimidazol-2-ylcarbamate |
| D | 2-(2-furyl)benzimidazole structure | 2-(2-Furyl)benzimidazole |
| E | benzene with two ortho -NHCNHCOOCH$_3$ groups (C=S) | 1,2-Bis(3-methoxycarbonyl-2-thioureido)benzene |
| F | benzene with two ortho -NHCNHCOOC$_2$H$_5$ groups (C=S) | 1,2-Bis(3-ethoxycarbonyl-2-thioureido)benzene |
| G | benzene with ortho -NHCNHCOOCH$_3$ (C=S) and -NHP(=O)(S-CH$_3$)(OCH$_3$) groups | 2-(O,S—Dimethylphosphorylamino)-1-(3′-methoxycarbonyl-2′-thioureido)benzene |

TABLE 2-continued

| Compound | Structure | Name |
|---|---|---|
| H | (phenyl ring with ortho substituents: NHC(=S)NHCOOCH₃ and NHP(=S)(OCH₃)(OCH₃)) | 2-(O,O—Dimethylthio-phosphorylamino)-1-(3'-methoxycarbonyl-2'-thioureido)benzene |
| I | 3,5-dichlorophenyl-N attached to 1,2-dimethylcyclopropane-1,2-dicarboximide | N—(3',5'-Dichloro-phenyl)-1,2-dimethyl-cyclopropane-1,2-di-carboximide |
| J | 3,5-dichlorophenyl-imidazolidine-2,4-dione with N—C(=O)—NHCH(CH₃)₂ substituent | 3-(3',5'-Dichloro-phenyl)-1-isopropyl-carbamoylimida-zolidin-2,4-dione |
| K | 3,5-dichlorophenyl-oxazolidine-2,4-dione with CH=CH₂ and CH₃ substituents | 3-(3',5'-Dichloro-phenyl)-5-methyl-5-vinyloxazolidin-2,4-dione |
| L | 3,5-dichlorophenyl-oxazolidine with COOC₂H₅ and CH₃ substituents | Ethyl (RS)—3-(3',5'-dichlorophenyl)-5-methyl-2,4-dioxo-oxazolidine-5-carboxylate |

Besides, the N-phenylcarbamates (I) may be also used in admixture with other fungicides, herbicides, insecticides, miticides, fertilizers, etc.

When the N-phenylcarbamates (I) are used as fungicides, they may be applied in such amounts as 2 to 100 grams per 10 ares. However, this amount may vary depending upon preparation forms, application times, application methods, application sites, diseases, crops and so on, and therefore, they are not limited to these particular amounts.

Some practical embodiments of the fungicidal composition according to the invention are illustratively shown in the following Examples wherein % and part(s) are by weight.

PREPARATION EXAMPLE 1

Two parts of Compound No. 21, 88 parts of clay and 10 parts of talc were thoroughly pulverized and mixed together to obtain a dust preparation containing 2% of the active ingredient.

PREPARATION EXAMPLE 2

Thirty parts of Compound No. 11, 45 parts of diatomaceous earth, 20 parts of white carbon, 3 parts of sodium laurylsulfate as a wetting agent and 2 parts of calcium ligninsulfonate as a dispersing agent were mixed while being powdered to obtain a wettable powder preparation containing 30% of the active ingredient.

PREPARATION EXAMPLE 3

Fifty parts of Compound No. 13, 45 parts of diatomaceous earth, 2.5 parts of calcium alkylbenzenesulfonate as a wetting agent and 2.5 parts of calcium ligninsulfonate as a dispersing agent were mixed while being powdered to obtain a wettable powder preparation containing 50% of the active ingredient.

PREPARATION EXAMPLE 4

Ten parts of Compound No. 46, 80 parts of cyclohexanone and 10 parts of polyoxyethylene alkylaryl ether as an emulsifier were mixed together to obtain an emulsifiable concentrate preparation containing 10% of the active ingredient.

PREPARATION EXAMPLE 5

One part of Compound No. 7, 1 part of Compound I, 88 parts of clay and 10 parts of talc were thoroughly pulverized and mixed together to obtain a dust preparation containing 2% of the active ingredient.

PREPARATION EXAMPLE 6

Twenty parts of Compound No. 86, 10 parts of Compound J, 45 parts of diatomaceous earth, 20 parts of white carbon, 3 parts of sodium laurylsulfate as a wetting agent and 2 parts of calcium ligninsulfonate as a dispersing agent were mixed while being powdered to obtain a wettable powder preparation containing 30% of the active ingredient.

PREPARATION EXAMPLE 7

Ten parts of Compound No. 88, 40 parts of Compound B, 45 parts of diatomaceous earth, 2.5 parts of calcium alkylbenzenesulfonate as a wetting agent and 2.5 parts of calcium ligninsulfonate as a dispersing agent were mixed while being powdered to obtain a wettable powder preparation containing 50% of the active ingredient.

PREPARATION EXAMPLE 8

Twenty-five parts of Compound No. 94, 50 parts of Compound I, 18 parts of diatomaceous earth, 3.5 parts of calcium alkylbenzenesulfonate as a wetting agent and 3.5 parts of calcium ligninsulfonate as a dispersing agent were mixed while being powdered to obtain a wettable powder preparation containing 75% of the active ingredient.

PREPARATION EXAMPLE 9

Twenty parts of Compound No. 50, 30 parts of Compound A, 40 parts of powdery sucrose, 5 parts of white carbon, 3 parts of sodium laurylsulfate as a wetting agent and 2 parts of calcium ligninsulfonate as a dispersing agent were mixed while being powdered to obtain a wettable powder preparation containing 50% of the active ingredient.

Typical test data indicating the excellent fungicidal activity of the N-phenylcarbamates (I) are shown below. The compounds used for comparison are as follows:

| Compound | Remarks |
|---|---|
| Swep (Cl,Cl-phenyl-NHCOCH$_3$) | Commercially available herbicide |
| Chlorpropham (Cl-phenyl-NHCOCH(CH$_3$)$_2$) | Commercially available herbicide |
| Barban (Cl-phenyl-NHCOCH$_2$C≡CCH$_2$Cl) | Commercially available herbicide |
| CEPC (Cl-phenyl-NHCOCH$_2$CH$_2$Cl) | Commercially available herbicide |
| Propham | |
| Chlorbufam (phenyl-NHCOCH(CH$_3$)$_2$) | Commercially available herbicide |
| Chlorbufam (Cl-phenyl-NHCOCH(C≡CH)CH$_3$) | Commercially available herbicide |
| Benomyl (benzimidazole-CONHC$_4$H$_9$, NHCOOCH$_3$) | Commercially available fungicide |
| Thiophanate-methyl (phenyl-NHC(S)NHCOOCH$_3$ ×2) | Commercially available fungicide |
| Carbendazim (benzimidazole-NHCOOCH$_3$) | Commercially available fungicide |
| Thiabendazole (benzimidazole-thiazole) | Commercially available fungicide |

EXPERIMENT 1

Protective activity test on powdery mildew of cucumber (*Sphaerotheca fuliginea*)

A flower pot of 90 ml volume was filed with sandy soil, and seeds of cucumber (var: Sagami-hanjiro) were sowed therein. Cultivation was carried out in a greenhouse for 8 days. Onto the resulting seedlings having cotyledons, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Sphaerotheca fuliginea* by spraying and further cultivated in the greenhouse. Ten days thereafter, the infectious state of the plants was observed. The degree of damage was determined in the following manner, and the results are shown in Table 3.

The leaves examined were measured for a percentage of infected area and classified into the corresponding disease indices, 0, 0.5, 1, 2, 4:

| Desease index | Percentage of infected area |
| --- | --- |
| 0 | No infection |
| 0.5 | Infected area of less than 5% |
| 1 | Infected area of less than 20% |
| 2 | Infected area of less than 50% |
| 4 | Infected area of not less than 50% |

The disease severity was calculated according to the following equation:

$$\text{Disease severity (\%)} = \frac{\Sigma \text{(Disease index)} \times \text{(Number of leaves)}}{4 \times \text{(Total number of leaves examined)}} \times 100$$

The prevention value was calculated according to the following equation:

$$\text{Prevention value (\%)} = 100 - \frac{\text{(Disease severity in treated plot)}}{\text{(Disease severity in untreated plot)}} \times 100$$

TABLE 3

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 200 | 100 | 0 |
| 2 | 200 | 100 | 0 |
| 3 | 200 | 100 | 0 |
| 4 | 200 | 92 | 0 |
| 5 | 200 | 100 | 0 |
| 6 | 200 | 100 | 0 |
| 7 | 200 | 100 | 32 |
| 8 | 200 | 100 | 0 |
| 9 | 200 | 100 | 0 |
| 10 | 200 | 100 | 0 |
| 11 | 200 | 100 | 0 |
| 12 | 200 | 100 | 0 |
| 13 | 200 | 100 | 0 |
| 14 | 200 | 100 | 0 |
| 15 | 200 | 100 | 0 |
| 16 | 200 | 100 | 0 |
| 17 | 200 | 100 | 0 |
| 18 | 200 | 100 | 0 |
| 19 | 200 | 100 | 0 |
| 20 | 200 | 100 | 0 |
| 21 | 200 | 100 | 0 |
| 22 | 200 | 100 | 0 |
| 23 | 200 | 90 | 0 |
| 24 | 200 | 100 | 0 |
| 25 | 200 | 100 | 0 |
| 26 | 200 | 100 | 0 |
| 27 | 200 | 100 | 0 |
| 28 | 200 | 100 | 0 |
| 29 | 200 | 100 | 0 |
| 30 | 200 | 100 | 0 |
| 31 | 200 | 100 | 0 |
| 32 | 200 | 100 | 0 |
| 33 | 200 | 84 | 0 |
| 34 | 200 | 100 | 0 |
| 35 | 200 | 100 | 26 |
| 36 | 200 | 97 | 0 |
| 37 | 200 | 100 | 0 |
| 38 | 200 | 100 | 34 |
| 39 | 200 | 100 | 0 |
| 40 | 200 | 100 | 0 |
| 41 | 200 | 100 | 0 |
| 42 | 200 | 82 | 0 |
| 43 | 200 | 100 | 0 |
| 44 | 200 | 100 | 0 |
| 45 | 200 | 100 | 0 |
| 46 | 200 | 100 | 0 |
| 47 | 200 | 100 | 0 |
| 48 | 200 | 100 | 0 |
| 49 | 200 | 100 | 0 |
| 50 | 200 | 100 | 0 |
| 51 | 200 | 100 | 0 |
| 52 | 200 | 100 | 0 |
| 53 | 200 | 100 | 0 |
| 54 | 200 | 100 | 0 |
| 55 | 200 | 90 | 0 |
| 56 | 200 | 100 | 0 |
| 57 | 200 | 100 | 0 |
| 58 | 200 | 100 | 0 |
| 59 | 200 | 100 | 0 |
| 60 | 200 | 100 | 0 |
| 61 | 200 | 100 | 0 |
| 62 | 200 | 100 | 0 |
| 63 | 200 | 100 | 0 |
| 64 | 200 | 100 | 0 |
| 65 | 200 | 86 | 0 |
| 66 | 200 | 100 | 0 |
| 67 | 200 | 100 | 52 |
| 68 | 200 | 100 | 23 |
| 69 | 200 | 88 | 0 |
| 70 | 200 | 100 | 0 |
| 71 | 200 | 100 | 0 |
| 72 | 200 | 100 | 0 |
| 73 | 200 | 100 | 0 |
| 74 | 200 | 100 | 0 |
| 75 | 200 | 100 | 0 |
| 76 | 200 | 100 | 0 |
| 77 | 200 | 90 | 0 |
| 78 | 200 | 92 | 0 |
| 79 | 200 | 94 | 0 |
| 80 | 200 | 100 | 0 |
| 81 | 200 | 100 | 0 |
| 82 | 200 | 100 | 0 |
| 83 | 200 | 100 | 0 |
| 84 | 200 | 97 | 0 |
| 85 | 200 | 94 | 0 |
| 86 | 200 | 100 | 0 |
| 87 | 200 | 100 | 0 |
| 88 | 200 | 100 | 0 |
| 89 | 200 | 92 | 0 |
| 90 | 200 | 88 | 0 |
| 91 | 200 | 84 | 0 |
| 92 | 200 | 88 | 0 |
| 93 | 200 | 90 | 0 |
| 94 | 200 | 100 | 0 |
| 95 | 200 | 100 | 0 |
| 96 | 200 | 100 | 0 |
| 97 | 200 | 100 | 0 |
| 98 | 200 | 100 | 0 |
| 99 | 200 | 100 | 0 |
| 100 | 200 | 100 | 0 |
| 101 | 200 | 98 | 0 |
| 102 | 200 | 100 | 0 |
| 103 | 200 | 100 | 0 |
| 104 | 200 | 86 | 0 |
| 105 | 200 | 84 | 0 |
| 106 | 200 | 94 | 0 |
| 107 | 200 | 90 | 0 |
| 108 | 200 | 88 | 0 |
| 109 | 200 | 88 | 0 |
| Swep | 200 | 0 | 0 |
| Chlorpropham | 200 | 0 | 0 |
| Barban | 200 | 25 | 0 |
| CEPC | 200 | 0 | 0 |
| Propham | 200 | 0 | 0 |
| Chlorbufam | 200 | 0 | 0 |
| Benomyl | 200 | 0 | 100 |
| Thiophanate-methyl | 200 | 0 | 100 |
| Carbendazim | 200 | 0 | 100 |

As understood from the results shown in Table 3, the N-phenylkcarbamates (I) of the invention show an excellent preventive effect on the drug-resistant strain but do not show any preventive effect on the tested drug-sensitive strain. To the contrary, commercially available known fungicides such as Benomyl, Thiophanate-methyl and Carbendazim show a notable controlling effect on the drug-sensitive strain but not on the drug-resistant strain. Other tested compounds structurally similar to the N-phenylcarbamates (I) do not show any fungicidal activity on the drug-sensitive strain and the drug-resistant strain.

EXPERIMENT 2

Preventive effect on cercospora leaf spot of sugarbeet (*Cercospora beticola*)

A flower pot of 90 ml volume was filled with sandy soil, and seeds of sugarbeet (var: Detroit dark red) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Cercospora beticola* by spraying. The pot was covered with a polyvinyl chloride sheet to make a condition of high humidity, and cultivation was continued in the greenhouse for 10 days. The degree of damage was determined in the same manner as in Experiment 1, and the results are shown in Table 4.

TABLE 4

| Compound No. | Concentration of active ingredient (ppm) | Prevention value when inoculated with drug-resistant strain (%) | Prevention value when inoculated with drug-sensitive strain (%) |
| --- | --- | --- | --- |
| 2 | 200 | 100 | 0 |
| 11 | 200 | 100 | 0 |
| 12 | 200 | 100 | 0 |
| 13 | 200 | 100 | 0 |
| 14 | 200 | 100 | 0 |
| 15 | 200 | 100 | 0 |
| 16 | 200 | 100 | 0 |
| 17 | 200 | 100 | 0 |
| 21 | 200 | 100 | 0 |
| 24 | 200 | 100 | 0 |
| 25 | 200 | 100 | 0 |
| 27 | 200 | 100 | 0 |
| 28 | 200 | 100 | 0 |
| 30 | 200 | 100 | 0 |
| 31 | 200 | 100 | 0 |
| 32 | 200 | 100 | 0 |
| 35 | 200 | 100 | 0 |
| 36 | 200 | 100 | 0 |
| 38 | 200 | 100 | 0 |
| 39 | 200 | 100 | 0 |
| 40 | 200 | 100 | 0 |
| 42 | 200 | 88 | 0 |
| 43 | 200 | 94 | 0 |
| 46 | 200 | 100 | 0 |
| 50 | 200 | 97 | 0 |
| 52 | 200 | 100 | 0 |
| 53 | 200 | 100 | 0 |
| 56 | 200 | 100 | 0 |
| 60 | 200 | 100 | 0 |
| 61 | 200 | 100 | 0 |
| 62 | 200 | 100 | 0 |
| 68 | 200 | 100 | 0 |
| 73 | 200 | 100 | 0 |
| 75 | 200 | 100 | 0 |
| 76 | 200 | 100 | 0 |
| 80 | 200 | 100 | 0 |
| 81 | 200 | 100 | 0 |
| 83 | 200 | 100 | 0 |
| 86 | 200 | 100 | 0 |
| 87 | 200 | 100 | 0 |
| 88 | 200 | 100 | 0 |
| 94 | 200 | 100 | 0 |
| 95 | 200 | 100 | 0 |
| 96 | 200 | 97 | 0 |
| 98 | 200 | 100 | 0 |
| 99 | 200 | 100 | 0 |
| 100 | 200 | 100 | 0 |
| 101 | 200 | 100 | 0 |
| 102 | 200 | 100 | 0 |
| Swep | 200 | 0 | 0 |
| Chlorpropham | 200 | 0 | 0 |
| Barban | 200 | 34 | 0 |
| CEPC | 200 | 0 | 0 |
| Propham | 200 | 0 | 0 |
| Chlorbufam | 200 | 0 | 0 |
| Benomyl | 200 | 0 | 100 |
| Thiophanate-methyl | 200 | 0 | 100 |
| Carbendazim | 200 | 0 | 100 |

As understood from the results shown in Table 4, the N-phenylcarbamates (I) of the invention show an excellent preventive effect on the drug-resistant strain but do not show any preventive effect on the tested drug-sensitive strain. To the contrary, commecially available known fungicides such as Benomyl and Thiophanate-methyl show a notable controlling effect on the drug-sensitive strain but not on the drug-resistant strain. Other tested compounds structurally similar to the N-phenylcarbamates (I) do not show any fungicidal activity on the drug-sensitive strain and the drug-resistant strain.

EXPERIMENT 3

Preventive effect on scab of pear (*Venturia nashicola*)

A plastic pot of 90 ml volume was filled with sandy soil, and seeds of pear (var: Chojuro) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Venturia nashicola* by spraying. The resulting plants were placed at 20° C. under a condition of high humidity for 3 days and then at 20° C. under irradiation with a fluorescent lamp for 20 days. The degree of damage was determined in the same manner as in Experiment 1, and the results are shown in Table 5.

TABLE 5

| Compound No. | Concentration of active ingredient (ppm) | Prevention value when inoculated with drug-resistant strain (%) | Prevention value when inoculated with drug-sensitive strain (%) |
| --- | --- | --- | --- |
| 2 | 200 | 100 | 0 |
| 3 | 200 | 100 | 0 |
| 7 | 200 | 100 | 0 |
| 11 | 200 | 100 | 0 |
| 12 | 200 | 100 | 0 |
| 13 | 200 | 100 | 0 |
| 14 | 200 | 100 | 0 |

TABLE 5-continued

| Compound No. | Concentration of active ingredient (ppm) | Prevention value when inoculated with drug-resistant strain (%) | Prevention value when inoculated with drug-sensitive strain (%) |
| --- | --- | --- | --- |
| 15 | 200 | 100 | 0 |
| 16 | 200 | 100 | 0 |
| 17 | 200 | 100 | 0 |
| 21 | 200 | 100 | 0 |
| 24 | 200 | 100 | 0 |
| 25 | 200 | 100 | 0 |
| 27 | 200 | 100 | 0 |
| 28 | 200 | 100 | 0 |
| 35 | 200 | 100 | 0 |
| 36 | 200 | 97 | 0 |
| 42 | 200 | 91 | 0 |
| 43 | 200 | 100 | 0 |
| 46 | 200 | 100 | 0 |
| 50 | 200 | 100 | 0 |
| 53 | 200 | 100 | 0 |
| 56 | 200 | 100 | 0 |
| 68 | 200 | 100 | 0 |
| 75 | 200 | 100 | 0 |
| 76 | 200 | 97 | 0 |
| 80 | 200 | 100 | 0 |
| 81 | 200 | 100 | 0 |
| 83 | 200 | 97 | 0 |
| 86 | 200 | 100 | 0 |
| 87 | 200 | 100 | 0 |
| 88 | 200 | 100 | 0 |
| 94 | 200 | 100 | 0 |
| 95 | 200 | 97 | 0 |
| 96 | 200 | 94 | 0 |
| 97 | 200 | 97 | 0 |
| 98 | 200 | 100 | 0 |
| 99 | 200 | 100 | 0 |
| 100 | 200 | 100 | 0 |
| 101 | 200 | 97 | 0 |
| 102 | 200 | 100 | 0 |
| Benomyl | 200 | 0 | 100 |
| Thiophanate-methyl | 200 | 0 | 100 |

As understood from the results shown in Table 5, the N-phenylcarbamates (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 4

Preventive effect on brown leaf-spot of peanut (Cercospora arachidicola)

A plastic pot of 90 ml volume was filled with sandy soil, and seeds of peanut (var: Chiba hanryusei) were sowed therein. Cultivation was carried out in a greenhouse for 14 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of Cercospora arachidicola by spraying. The resulting plants were covered with a polyvinyl chloride sheet to make a condition of humidity and cultivated in the greenhouse for 10 days. The degree of damage was determined in the same manner as in Experiment 1, and the results are shown in Table 6.

TABLE 6

| Compound No. | Concentration of active ingredient (ppm) | Prevention value when inoculated with drug-resistant strain (%) | Prevention value when inoculated with drug-sensitive strain (%) |
| --- | --- | --- | --- |
| 2 | 200 | 100 | 0 |
| 7 | 200 | 100 | 0 |
| 12 | 200 | 100 | 0 |
| 13 | 200 | 100 | 0 |
| 17 | 200 | 100 | 0 |
| 25 | 200 | 100 | 0 |
| 27 | 200 | 100 | 0 |
| 28 | 200 | 100 | 0 |
| 31 | 200 | 100 | 0 |
| 32 | 200 | 100 | 0 |
| 35 | 200 | 100 | 0 |
| 38 | 200 | 100 | 0 |
| 39 | 200 | 100 | 0 |
| 40 | 200 | 100 | 0 |
| 46 | 200 | 100 | 0 |
| 50 | 200 | 100 | 0 |
| 53 | 200 | 100 | 0 |
| 56 | 200 | 100 | 0 |
| 60 | 200 | 100 | 0 |
| 62 | 200 | 100 | 0 |
| 64 | 200 | 100 | 0 |
| 73 | 200 | 100 | 0 |
| 76 | 200 | 100 | 0 |
| 86 | 200 | 100 | 0 |
| 87 | 200 | 100 | 0 |
| 88 | 200 | 100 | 0 |
| 94 | 200 | 100 | 0 |
| 98 | 200 | 100 | 0 |
| 99 | 200 | 100 | 0 |
| 100 | 200 | 100 | 0 |
| Benomyl | 200 | 0 | 100 |
| Thiophanate-methyl | 200 | 0 | 100 |

As understood from the results shown in Table 6, the N-phenylcarbamates (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 5

Preventive effect on gray mold of cucumber (Botrytis cinerea)

Plastic pots of 90 ml volume was filled with sandy soil, and seeds of cucumber (var: Sagami-hanjiro) were sowed therein. Cultivation was carried out in a greenhouse for 8 days to obtain cucumber seedlings expanding cotyledons. Onto the resulting seedlings, the test compound formulated in emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of Botrytis cinerea by putting them on the leaf surfaces. After the plants were infected by incubating under high humidity at 20° C. for 3 days, the rates of disease severity were observed. The degree of damage was determined in the same manner as in Experiment 1, and the results are shown in Table 7.

TABLE 7

| Compound No. | Concentration of active ingredient (ppm) | Prevention value when inoculated with drug-resistant strain (%) | Prevention value when inoculated with drug-sensitive strain (%) |
|---|---|---|---|
| 1 | 200 | 100 | 0 |
|   | 50 | 94 | 0 |
| 2 | 200 | 100 | 0 |
|   | 50 | 100 | 0 |
| 3 | 200 | 100 | 0 |
|   | 50 | 94 | 0 |
| 4 | 500 | 98 | 0 |
| 5 | 200 | 100 | 0 |
| 6 | 200 | 91 | 0 |
| 7 | 200 | 100 | 0 |
|   | 50 | 100 | 0 |
| 8 | 200 | 100 | 0 |
| 9 | 200 | 100 | 0 |
| 10 | 500 | 98 | 0 |
| 11 | 200 | 97 | 0 |
| 12 | 200 | 100 | 0 |
|   | 50 | 97 | 0 |
| 13 | 200 | 100 | 0 |
|   | 50 | 100 | 0 |
|   | 12.5 | 100 | 0 |
| 14 | 200 | 100 | 0 |
|   | 50 | 100 | 0 |
| 15 | 200 | 100 | 0 |
|   | 50 | 100 | 0 |
|   | 12.5 | 100 | 0 |
| 16 | 200 | 100 | 0 |
|   | 50 | 100 | 0 |
| 17 | 200 | 100 | 0 |
|   | 50 | 100 | 0 |
| 18 | 200 | 97 | 0 |
| 19 | 200 | 100 | 0 |
| 20 | 200 | 100 | 0 |
| 21 | 200 | 100 | 0 |
|   | 50 | 100 | 0 |
| 22 | 200 | 97 | 0 |
| 23 | 500 | 96 | 0 |
| 24 | 200 | 100 | 0 |
| 25 | 200 | 100 | 0 |
|   | 50 | 100 | 0 |
|   | 12.5 | 100 | 0 |
| 26 | 200 | 100 | 0 |
| 27 | 200 | 100 | 0 |
|   | 50 | 100 | 0 |
| 28 | 200 | 100 | 0 |
|   | 50 | 100 | 0 |
|   | 12.5 | 94 | 0 |
| 29 | 200 | 100 | 0 |
|   | 50 | 100 | 0 |
| 30 | 200 | 100 | 0 |
|   | 50 | 100 | 0 |
| 31 | 200 | 100 | 0 |
|   | 50 | 100 | 0 |
| 32 | 200 | 100 | 0 |
|   | 50 | 100 | 0 |
| 33 | 500 | 86 | 0 |
| 34 | 200 | 100 | 0 |
| 35 | 200 | 100 | 0 |
|   | 50 | 100 | 0 |
| 36 | 200 | 100 | 0 |
| 37 | 200 | 100 | 0 |
| 38 | 200 | 100 | 0 |
|   | 50 | 100 | 0 |
| 39 | 200 | 100 | 0 |
|   | 50 | 100 | 0 |
| 40 | 200 | 100 | 0 |
|   | 50 | 100 | 0 |
| 41 | 200 | 94 | 0 |
| 42 | 500 | 82 | 0 |
| 43 | 200 | 100 | 0 |
|   | 50 | 100 | 0 |
|   | 12.5 | 94 | 0 |
| 44 | 200 | 100 | 0 |
| 45 | 200 | 91 | 0 |
| 46 | 200 | 100 | 0 |
|   | 50 | 100 | 0 |
| 47 | 200 | 100 | 0 |
| 48 | 200 | 100 | 0 |
| 49 | 200 | 100 | 0 |
| 50 | 200 | 100 | 0 |
|   | 50 | 100 | 0 |
| 51 | 200 | 100 | 0 |
|   | 50 | 100 | 0 |
| 52 | 200 | 100 | 0 |
|   | 50 | 100 | 0 |
| 53 | 200 | 100 | 0 |
|   | 50 | 100 | 0 |
| 54 | 200 | 95 | 0 |
| 55 | 500 | 97 | 0 |
| 56 | 200 | 100 | 0 |
|   | 50 | 100 | 0 |
| 57 | 200 | 97 | 0 |
| 58 | 200 | 97 | 0 |
| 59 | 200 | 100 | 0 |
| 60 | 200 | 100 | 0 |
| 61 | 200 | 100 | 0 |
|   | 50 | 100 | 0 |
| 62 | 200 | 100 | 0 |
|   | 50 | 100 | 0 |
| 63 | 200 | 100 | 0 |
|   | 50 | 100 | 0 |
| 64 | 200 | 100 | 0 |
|   | 50 | 100 | 0 |
| 65 | 500 | 87 | 0 |
| 66 | 200 | 100 | 0 |
| 67 | 200 | 100 | 0 |
| 68 | 200 | 100 | 0 |
| 69 | 500 | 95 | 0 |
| 70 | 200 | 100 | 0 |
| 71 | 200 | 97 | 0 |
| 72 | 200 | 97 | 0 |
| 73 | 200 | 97 | 0 |
| 74 | 200 | 100 | 0 |
| 75 | 200 | 100 | 0 |
| 76 | 200 | 100 | 0 |
| 77 | 500 | 97 | 0 |
| 78 | 200 | 100 | 0 |
| 79 | 200 | 100 | 0 |
| 80 | 200 | 100 | 0 |
| 81 | 200 | 100 | 0 |
| 82 | 200 | 100 | 0 |
| 83 | 200 | 100 | 0 |
|   | 50 | 92 | 0 |
| 84 | 200 | 100 | 0 |
| 85 | 200 | 97 | 0 |
| 86 | 200 | 100 | 0 |
|   | 50 | 100 | 0 |
|   | 12.5 | 97 | 0 |
| 87 | 200 | 100 | 0 |
|   | 50 | 97 | 0 |
|   | 12.5 | 86 | 0 |
| 88 | 200 | 100 | 0 |
|   | 50 | 100 | 0 |
|   | 12.5 | 88 | 0 |
| 89 | 200 | 94 | 0 |
| 90 | 200 | 88 | 0 |
| 91 | 200 | 92 | 0 |
| 92 | 200 | 92 | 0 |
| 93 | 200 | 94 | 0 |
| 94 | 200 | 100 | 0 |
|   | 50 | 97 | 0 |
|   | 12.5 | 94 | 0 |
| 95 | 200 | 100 | 0 |
|   | 50 | 97 | 0 |
| 96 | 200 | 100 | 0 |
|   | 50 | 94 | 0 |
| 97 | 200 | 100 | 0 |
|   | 50 | 94 | 0 |
| 98 | 200 | 100 | 0 |
|   | 50 | 100 | 0 |
|   | 12.5 | 97 | 0 |
| 99 | 200 | 100 | 0 |
|   | 50 | 97 | 0 |

TABLE 7-continued

| Compound No. | Concentration of active ingredient (ppm) | Prevention value when inoculated with drug-resistant strain (%) | Prevention value when inoculated with drug-sensitive strain (%) |
| --- | --- | --- | --- |
|  | 12.5 | 94 | 0 |
| 100 | 200 | 100 | 0 |
|  | 50 | 97 | 0 |
|  | 12.5 | 97 | 0 |
| 101 | 200 | 100 | 0 |
|  | 50 | 94 | 0 |
| 102 | 200 | 100 | 0 |
|  | 50 | 97 | 0 |
| 103 | 200 | 100 | 0 |
|  | 50 | 94 | 0 |
| 104 | 200 | 97 | 0 |
| 105 | 200 | 97 | 0 |
| 106 | 200 | 100 | 0 |
| 107 | 200 | 100 | 0 |
| 108 | 200 | 100 | 0 |
| 109 | 200 | 97 | 0 |
| Benomyl | 200 | 0 | 100 |
| Thiophanate-methyl | 200 | 0 | 100 |

As understood from the results shown in Table 7, the N-phenylcarbamates (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 6

Preventive effect on gummy stem blight of cucumber (*Mycosphaerella melonis*)

Plastic pots of 90 ml volume was filled with sandy soil, and seeds of cucumber (var: Sagami-hanjiro) were sowed therein. Cultivation was carried out in a greenhouse for 8 days to obtain cucumber seedlings expanding cotyledons. Onto the resulting seedlings, the test compound formulated in emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of *Mycosphaerella melonis* by putting them on the leaf surfaces. After the plants were infected by incubating under high humidity at 25° C. for 4 days, the rates of disease severity were observed. The degree of damage was determined in the same manner as in Experiment 1, and the results are shown in Table 8.

TABLE 8

| Compound No. | Concentration of active ingredient (ppm) | Prevention inoculated with drug-resistant strain (%) | Prevention inoculated with drug-sensitive strain (%) |
| --- | --- | --- | --- |
| 3 | 200 | 100 | 0 |
| 7 | 200 | 100 | 0 |
| 12 | 200 | 100 | 0 |
| 13 | 200 | 100 | 0 |
| 14 | 200 | 100 | 0 |
| 16 | 200 | 100 | 0 |
| 28 | 200 | 100 | 0 |
| 36 | 200 | 100 | 0 |
| 46 | 200 | 100 | 0 |
| 48 | 200 | 100 | 0 |
| 49 | 200 | 100 | 0 |
| 53 | 200 | 100 | 0 |
| 56 | 200 | 100 | 0 |
| 61 | 200 | 100 | 0 |
| 63 | 200 | 100 | 0 |
| 74 | 200 | 100 | 0 |
| 76 | 200 | 100 | 0 |
| 86 | 200 | 100 | 0 |
| 87 | 200 | 100 | 0 |
| 88 | 200 | 100 | 0 |
| 94 | 200 | 100 | 0 |
| 98 | 200 | 100 | 0 |
| 99 | 200 | 100 | 0 |
| 100 | 200 | 100 | 0 |
| Benomyl | 200 | 0 | 100 |
| Thiophanate-methyl | 200 | 0 | 100 |

As understood from the results shown in Table 8, the N-phenylcarbamates (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 7

Preventive effect on green mold of orange (*Penicillium italicum*)

Fruits of orange (var: Unshu) were washed with water and dried in the air. The fruits were immersed in a solution of the test compound prepared by diluting an emulsifiable concentrate comprising the test compound with water for 1 minute. After drying in the air, the fruits were inoculated with a spore suspension of the drug-resistant or drug-sensitive strain of *Penicillium italicum* by spraying and placed in a room of high humidity for 14 days. The degree of damage was determined in the following manner:

The fruits examined were measured for a percentage of infected area and classified into the corresponding indices, 0, 1, 2, 3, 4, 5:

| Disease index | Percentage of infected area |
| --- | --- |
| 0 | No infection |
| 1 | Infected area of less than 20% |
| 2 | Infected area of less than 40% |
| 3 | Infected area of less than 60% |
| 4 | Infected area of less than 80% |
| 5 | Infected area of not less than 80% |

Calculation of the degree of damage and the prevention value was made as in Experiment 1.

The results are shown in Table 9.

TABLE 9

| Compound No. | Concentration of active ingredient (ppm) | Prevention value when inoculated with drug-resistant strain (%) | Prevention value when inoculated with drug-sensitive strain (%) |
| --- | --- | --- | --- |
| 2 | 200 | 100 | 0 |
| 5 | 200 | 100 | 0 |
| 9 | 200 | 100 | 0 |
| 11 | 200 | 100 | 0 |

TABLE 9-continued

| Compound No. | Concentration of active ingredient (ppm) | Prevention value when inoculated with drug-resistant strain (%) | Prevention value when inoculated with drug-sensitive strain (%) |
| --- | --- | --- | --- |
| 13 | 200 | 100 | 0 |
| 21 | 200 | 100 | 0 |
| 28 | 200 | 97 | 0 |
| 46 | 200 | 100 | 0 |
| 50 | 200 | 100 | 0 |
| 53 | 200 | 100 | 0 |
| 56 | 200 | 100 | 0 |
| 61 | 200 | 100 | 0 |
| 62 | 200 | 100 | 0 |
| 63 | 200 | 100 | 0 |
| 64 | 200 | 100 | 0 |
| 67 | 200 | 100 | 0 |
| 70 | 200 | 100 | 0 |
| 73 | 200 | 100 | 0 |
| 74 | 200 | 100 | 0 |
| 75 | 200 | 100 | 0 |
| 76 | 200 | 100 | 0 |
| 86 | 200 | 100 | 0 |
| 87 | 200 | 100 | 0 |
| 88 | 200 | 100 | 0 |
| 94 | 200 | 100 | 0 |
| 98 | 200 | 100 | 0 |
| 99 | 200 | 100 | 0 |
| 100 | 200 | 100 | 0 |
| Benomyl | 200 | 0 | 100 |
| Thiophanate-methyl | 200 | 0 | 100 |
| Thiabendazole | 200 | 0 | 100 |

As understood from the results shown in Table 9, the N-phenylcarbamates (I) of the invention show an excellent preventive effect on the drug-resistant strain but do not show any preventive effect on the tested drug-sensitive strain. To the contrary, commercially available known fungicides such as Benomyl, Thiophanate-methyl and Thiabendazole show a notable controlling effect on the drug-sensitive strain but not on the drug-resistant strain.

EXPERIMENT 8

Preventive effect on powdery mildew of cucumber (*Sphaerotheca fuliginea*)

A plastic pot of 90 ml volume was filled with sandy soil, and seeds of cucumber (var: Sagami-hanjiro) were sowed therein. Cultivation was carried out in a greenhouse for 8 days. Onto the resulting seedlings having cotyledons, the test compound(s) formulated in emulsifiable concentrate or wettable powder and diluted with water were sprayed at a rate of 10 ml per pot. Then, the seedlings were inoculated with a mixed spore suspension of the drug-resistant and drug-sensitive strain of *Sphaerotheca fuliginea* by spraying and further cultivated in the greenhouse. Ten days thereafter, the infectious state of the plants was observed. The degree of damage was determined in the same manner as in Experiment 1, and the results are shown in Table 10.

TABLE 10

| Compound No. | Concentration of active ingredient (ppm) | Prevention value (%) |
| --- | --- | --- |
| 13 | 100 | 34 |
| 13 | 20 | 0 |
| 15 | 100 | 28 |
| 15 | 20 | 0 |
| 28 | 100 | 44 |
| 28 | 20 | 0 |
| 43 | 100 | 36 |
| 43 | 20 | 0 |
| 86 | 100 | 44 |
| 86 | 20 | 0 |
| 88 | 100 | 28 |
| 88 | 20 | 0 |
| 94 | 100 | 32 |
| 94 | 20 | 0 |
| 98 | 100 | 28 |
| 98 | 20 | 0 |
| 99 | 100 | 28 |
| 99 | 20 | 0 |
| 100 | 100 | 36 |
| 100 | 20 | 0 |
| A | 100 | 45 |
| A | 20 | 12 |
| B | 500 | 42 |
| B | 100 | 10 |
| C | 100 | 42 |
| C | 20 | 8 |
| D | 500 | 36 |
| D | 100 | 0 |
| E | 100 | 44 |
| E | 20 | 10 |
| F | 100 | 43 |
| F | 20 | 8 |
| G | 100 | 42 |
| G | 20 | 8 |
| H | 100 | 40 |
| H | 20 | 5 |
| 13 + A | 20 + 20 | 100 |
| 13 + E | 20 + 20 | 100 |
| 13 + H | 20 + 20 | 100 |
| 15 + A | 20 + 20 | 100 |
| 15 + F | 20 + 20 | 100 |
| 28 + A | 20 + 20 | 100 |
| 28 + B | 20 + 20 | 100 |
| 28 + C | 20 + 20 | 100 |
| 43 + D | 20 + 20 | 100 |
| 43 + G | 20 + 20 | 100 |
| 43 + H | 20 + 20 | 100 |
| 86 + A | 20 + 20 | 100 |
| 86 + B | 20 + 20 | 100 |
| 86 + F | 20 + 20 | 100 |
| 88 + C | 20 + 20 | 100 |
| 88 + E | 20 + 20 | 100 |
| 88 + G | 20 + 20 | 100 |
| 94 + A | 20 + 20 | 100 |
| 94 + E | 20 + 20 | 100 |
| 94 + G | 20 + 20 | 100 |
| 98 + C | 20 + 20 | 100 |
| 98 + H | 20 + 20 | 100 |
| 99 + A | 20 + 20 | 100 |
| 99 + B | 20 + 20 | 100 |
| 100 + A | 20 + 20 | 100 |
| 100 + D | 20 + 20 | 100 |
| 100 + E | 20 + 20 | 100 |

As understood from the results shown in Table 10, the combined use of the N-phenylcarbamates (I) of the invention with benzimidazole thiophanate fungicides and/or cyclic imide fungicides show much more excellent preventive effect than their sole use.

EXPERIMENT 9

Preventive effect on gray mold of tomato (*Botrytis cinerea*)

A plastic pot of 90 ml volume was filled with sandy soil, and seeds of tomato (var: Fukuji No. 2) were sowed therein. Cultivation was carried out in a greenhouse for 4 weeks. Onto the resulting seedlings at the 4-leaf stage, the test compound(s) formulated in emulsifiable concentrate or wettable powder and diluted with water were sprayed at a rate of 10 ml per pot. Then, the seedlings were inoculated with a mixed spore suspension of the drug-resistant and drug-sensitive strain of *Botrytis cinerea* by spraying and placed at 20° C. in a room of high humidity for 5 days. The degree of damage was determined in the same manner as in Experiment 1, and the results are shown in Table 11.

TABLE 11

| Compound No. | Concentration of active ingredient (ppm) | Prevention value (%) |
|---|---|---|
| 13 | 100 | 44 |
| 13 | 20 | 0 |
| 25 | 100 | 27 |
| 25 | 20 | 0 |
| 28 | 100 | 38 |
| 28 | 20 | 0 |
| 43 | 100 | 38 |
| 43 | 20 | 0 |
| 86 | 100 | 42 |
| 86 | 20 | 0 |
| 88 | 100 | 42 |
| 88 | 20 | 0 |
| 94 | 100 | 42 |
| 94 | 20 | 0 |
| 98 | 100 | 40 |
| 98 | 20 | 0 |
| 99 | 100 | 44 |
| 99 | 20 | 0 |
| 100 | 100 | 38 |
| 100 | 20 | 0 |
| I | 100 | 48 |
| I | 20 | 22 |
| J | 500 | 46 |
| J | 100 | 18 |
| K | 100 | 42 |
| K | 20 | 15 |
| L | 500 | 42 |
| L | 100 | 12 |
| 13 + I | 20 + 50 | 100 |
| 13 + J | 20 + 50 | 100 |
| 13 + K | 20 + 50 | 100 |
| 13 + L | 20 + 50 | 100 |
| 25 + I | 20 + 50 | 100 |
| 25 + K | 20 + 50 | 100 |
| 28 + I | 20 + 50 | 100 |
| 28 + L | 20 + 50 | 100 |
| 43 + I | 20 + 50 | 100 |
| 43 + J | 20 + 50 | 100 |
| 86 + I | 20 + 50 | 100 |
| 86 + K | 20 + 50 | 100 |
| 88 + I | 20 + 50 | 100 |
| 88 + J | 20 + 50 | 100 |
| 94 + I | 20 + 50 | 100 |
| 94 + J | 20 + 50 | 100 |
| 98 + I | 20 + 50 | 100 |
| 98 + K | 20 + 50 | 100 |
| 99 + I | 20 + 50 | 100 |
| 99 + J | 20 + 50 | 100 |
| 100 + I | 20 + 50 | 100 |
| 100 + K | 20 + 50 | 100 |

As understood from the results shown in Table 11, the combined use of the N-phenylcarbamates (I) of the invention with benzimidazole thiophanate fungicides and/or cyclic imide fungicides show much more excellent preventive effect then their sole use.

What is claimed is:

1. A fungicidal composition which comprises as an active ingredient a fungicidally effective amount of an N-phenylcarbamate of the formula:

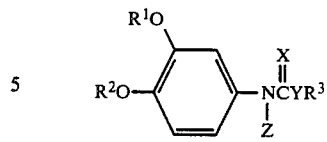

wherein $R^1$ and $R^2$ are, same or different, a lower alkyl group, a lower alkenyl group, a lower alkynyl group or a lower alkyl group substituted with at least one member selected from the group consisting of halogen, lower alkoxy and lower cycloalkyl; $R^3$ is a $C_1$–$C_8$ alkyl group, a $C_3$–$C_8$ alkenyl group, a $C_3$–$C_8$ alkynyl group, lower cycloalkyl group, a lower haloalkenyl group, a lower haloalkynyl group, a lower aralkyl group, a lower alkyl group substituted with at least one member selected from the group consisting of halogen, cyano, lower alkoxy, lower alkenyloxy, lower haloalkoxy, phenoxy, lower aralkyloxy and lower cycloalkyl, or a group of the formula:

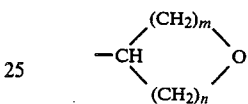

in which m is 0, 1 or 2, n is 1, 2 or 3; X and Y are, same or different, an oxygen atom or a sulfur atom; and Z is a hydrogen atom, a lower alkyl group, a lower alkenyl group, a lower alkynyl group, a lower cycloalkyl group, a lower haloalkenyl group, a lower alkyl group substituted with at least one member selected from the group consisting of halogen, cyano, lower alkoxy and lower alkoxycarbonyl, or a group of the formula: —$COR^4$ or —$SO_2R^4$ in which $R^4$ is a lower alkyl group, a lower alkenyl group, a lower alkynyl group, a lower cycloalkyl group, a lower haloalkenyl group, a lower alkyl group substituted with at least one member selected from the group consisting of halogen, cyano, lower alkoxy, lower cycloalkyl and phenoxy (phenoxy being optionally substituted with at least one halogen and/or at least one alkyl), a phenyl group, a furyl group, a thienyl group, a phenyl group substituted with at least one member selected from the group consisting of halogen, cyano, nitro, trifluoromethyl, lower alkyl and lower alkoxy, or an aralkyl group (aralkyl being optionally substituted with at least one halogen and/or at least one alkyl), with the proviso that when $R^1$ is methyl, $R^2$ is neither methyl nor butyl, and an inert carrier or diluent.

2. The fungicidal composition according to claim 1, which further comprises as an additional active ingredient(s) a benzimidazole thiophanate fungicide and/or a cyclic imide fungicide.

3. The fungicidal composition according to claim 2, wherein the benzimidazole thiophanate fungicide includes methyl 1-(butylcarbamoyl)benzimidazol-2-ylcarbamate, 2-(2-furyl)benzimidazole, 2-(4-thiazolyl)benzimidazole, methyl benzimidazol-2-ylcarbamate, 1,2-bis(3-methoxycarbonyl-2-thioureido)benzene, 1,2-bis(3-ethoxycarbonyl-2-thioureido)benzene, 2-(O,S-dimethylphosphorylamino)-1-(3'-methoxycarbonyl-2'-thioureido)benzene or 2-(O,O-dimethylthiophosphorylamino)-1-(3'-methoxycarbonyl-2'-thioureido)-benzene and said cyclic imide fungicide includes 3-(3',5'-dichlorophenyl)-1,2-dimethylcyclopropane-1,2-dicarboximide, 3-(3',5'-dichlorophenyl)-1-isopropylcarbamoylimidazolidine-2,4-dione, 3-(3',5'-dichlorophenyl)-5-methyl-5-vinyloxazoline-2,4-dione or ethyl (RS)-3-(3',5'-dichlorophenyl)-5-methyl-2,4-dioxooxazolidine-5-carboxylate.

4. An N-phenylcarbamate of the formula:

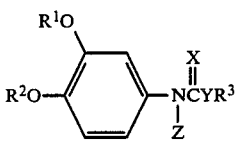

wherein $R^1$ and $R^2$ are, same or different, a lower alkyl group, a lower alkenyl group, a lower alkynyl group or a lower alkyl group substituted with at least one member selected from the group consisting of halogen, lower alkoxy and lower cycloalkyl; $R^3$ is a $C_1$–$C_8$ alkyl group, a $C_3$–$C_8$ alkenyl group, a $C_3$–$C_8$ alkynyl group, lower cycloalkyl group, a lower haloalkenyl group, a lower haloalkynyl group, a lower aralkyl group, a lower alkyl group substituted with at least one member selected from the group consisting of halogen, cyano, lower alkoxy, lower alkenyloxy, lower haloalkoxy, phenoxy, lower aralkyloxy and lower cycloalkyl, or a group of the formula

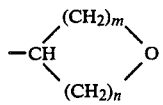

in which m is 0, 1 or 2, n is 1, 2 or 3; X and Y are, same or different, an oxygen atom or a sulfur atom; and Z is a hydrogen atom, a lower alkyl group, a lower alkenyl group, a lower alkynyl group, a lower cycloalkyl group, a lower haloalkenyl group, a lower alkyl group substituted with at least one member selected from the group consisting of halogen, cyano, lower alkoxy and lower alkoxycarbonyl, or a group of the formula: —$COR^4$ or —$SO_2R^4$ in which $R^4$ is a lower alkyl group, a lower alkenyl group, a lower alkynyl group, a lower cycloalkyl group, a lower haloalkenyl group, a lower alkyl group substituted with at least one member selected from the group consisting of halogen, cyano, lower alkoxy, lower cycloalkyl and phenoxy (phenoxy being optionally substituted with at least one halogen and/or at least one alkyl), a phenyl group, a furyl group, a thienyl group, a phenyl group substituted with at least one member selected from the group consisting of halogen, cyano, nitro, trifluoromethyl, lower alkyl and lower alkoxy, or an aralkyl group (aralkyl being optionally substituted with at least one halogen and/or at least one alkyl), with the proviso that when $R^1$ is methyl, $R^2$ is neither methyl nor butyl.

5. The N-phenylcarbamate according to claim 4, wherein $R^1$ and $R^2$ are independently methyl, ethyl, n-propyl, isopropyl, n-butyl, allyl, 2-butenyl, 3-butenyl, propargyl, 3-butynyl, difluoromethyl, 2-chloroethyl, 2,2,2-trifluoroethyl, 2-methoxyethyl or cyclopropylmethyl, $R^3$ is methyl, ethyl, n-propyl, isopropyl, sec-butyl, 1-ethylpropyl, 1-methylbutyl, 1-ethylbutyl, 2-butenyl, 3-butenyl, 2-methyl-2-propenyl, 1-ethyl-2-propenyl, 1-methyl-3-butenyl, 1-pentyl-2-propenyl, propargyl, 1-methyl-2-propynyl, 2-butynyl, 3-butynyl, 1-ethyl-2-propynyl, 1-methyl-3-butynyl, 1-butyl-2-propynyl, 1-pentyl-2-propynyl, cyclobutyl, cyclopentyl, 2-fluoroethyl, 2-chloroethyl, 2,2-dichloroethyl, 1-methyl-2-bromoethyl, 1-fluoromethyl-2-fluoroethyl, 1-bromoethyl-2-bromoethyl, 1-methyl-2,2,2-trichloroethyl, 1-ethyl-2-bromoethyl, 4-chloro-2-butenyl, 4-chloro-2-butynyl, 2-cyanoethyl, 1-methyl-2-methoxyethyl, 1-methyl-2-butoxyethyl, 2-allyloxyethyl, 2-(2-chloroethoxy)ethyl, 2-benzyloxyethyl, 1-chloromethyl-2-methoxyethyl, cyclopropylmethyl, 1-cyclopropylethyl, 1-cyclopentylethyl, 2-furylmethyl, 1-phenylethyl or 3-tetrahydrofuranyl; X and Y are independently oxygen or sulfur; and Z is hydrogen, methyl, ethyl, n-butyl, allyl, acetyl, propionyl, n-pentanoyl, sec-pentanoyl, cyclopropanecarbonyl, benzoyl, 2-chlorobenzoyl, 2,4-dichlorobenzoyl, 4-methylbenzoyl, methanesulfonyl or ethoxycarbonylmethyl, with the proviso that when $R^1$ is methyl, $R^2$ is neither methyl nor butyl.

6. The N-phenylcarbamate according to claim 5, wherein $R^1$ and $R^2$ are independently methyl, ethyl, n-propyl, allyl or propargyl, $R^3$ is ethyl, isopropyl, sec-butyl, 1-methylbutyl, 1-ethylpropyl, 1-ethylbutyl, 1-methyl-2-propenyl, 1-ethyl-2-propenyl, 1-methyl-3-butenyl, propargyl, 1-methyl-2-propynyl, 1-ethyl-2-propynyl, 3-butynyl, 1-methyl-3-butynyl, 1-butyl-2-propynyl, 2-fluoroethyl, 1-methyl-2-bromoethyl, 1-fluoromethyl-2-fluoroethyl, 1-bromomethyl-2-bromoethyl, 4-chloro-2-butynyl, 1-methyl-2-methoxyethyl, 1-cyclopropylethyl or 1-phenylethyl; X is oxygen, Y is oxygen or sulfur; and Z is hydrogen, acetyl, propionyl, n-pentanoyl, sec-pentanoyl, cyclopropanecarbonyl, benzoyl, 2-chlorobenzoyl, 2,4-dichlorobenzoyl or 4-methylbenzoyl, with the proviso that when $R^1$ is methyl, $R^2$ is not methyl.

7. The N-phenylcarbamate according to claim 6, wherein $R^1$ and $R^2$ are ethyl, $R^3$ is ethyl, isopropyl, sec-butyl, 1-methylbutyl, 1-ethylbutyl, 1-methyl-3-butenyl, 1-methyl-2-propynyl, 4-chloro-2-butynyl or 1-phenylethyl, X is oxygen, Y is oxygen or sulfur and Z is hydrogen, acetyl, cyclopropanecarbonyl, benzoyl or 2-chlorobenzoyl.

8. The N-phenylcarbamate according to claim 4, Isopropyl N-(3,4-diethoxyphenyl)carbamate.

9. The N-phenylcarbamate according to claim 4, 1-Methyl-2-propynyl N-(3,4-diethoxyphenyl)-carbamate.

10. The N-phenylcarbamate according to claim 4, 4-Chloro-2-butynyl N-(3,4-diethoxyphenyl)-carbamate.

11. The N-phenylcarbamate according to claim 4, Isopropyl N-(3,4-diethoxyphenyl)thiolcarbamate.

12. The N-phenylcarbamate according to claim 4, 1-Phenylethyl N-(3,4-diethoxyphenyl)carbamate.

13. The N-phenylcarbamate according to claim 4, Isopropyl N-acetyl-N-(3,4-diethoxyphenyl)-carbamate.

14. The N-phenylcarbamate according to claim 4, Isopropyl N-cyclopropanecarbonyl-N-(3,4-diethoxyphenyl)carbamate.

15. The N-phenylcarbamate according to claim 4, Isopropyl N-benzony-N-(3,4-diethoxyphenyl)-carbamate.

16. The N-phenylcarbamate according to claim 4, Isopropyl N-(2-chlorobenzoyl)-N-(3,4-diethoxyphenyl)carbamate.

17. A method for controlling plant pathogenic fungi which comprises applying a fungicidally effective amount of at least one of the N-phenylcarbamates of the formula:

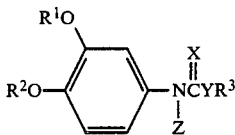

wherein $R^1$, $R^2$, $R^3$, X, Y and Z are each as defined in claim 1, to plant pathogenic fungi.

18. The method according to claim 17, wherein the plant pathogenic fungi is the drug-resistant strain.

19. A method for controlling plant pathogenic fungi which comprises applying a fungicidally effective amount of a mixture of the N-phenylcarbamate of the formula:

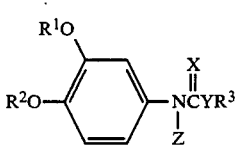

wherein $R^1$, $R^2$, $R^3$, X, Y and Z are each as defined in claim 1 and a benzimidazole thiophanate fungicide and/or a cyclic imide fungicide.

20. A process for producing an N-phenylcarbamate of the formula:

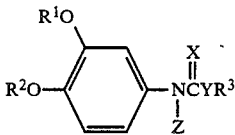

wherein Z is as defined in claim 4 except hydrogen and $R^1$, $R^2$, $R^3$, X and Y are each as defined in claim 4, which comprises reacting a 3,4-dialkoxyphenylcarbamate of the formula:

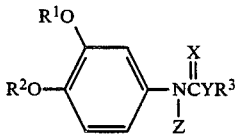

wherein $R^1$, $R^2$, $R^3$, X and Y are each as defined above, with a halide of the formula:

A—Z wherein A is a halogen atom and Z is as defined above.

21. A fungicidal composition which comprises as an active ingredient a fungicidally effective amount of an N-phenylcarbamate of the formula:

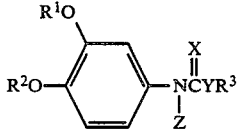

wherein $R^1$ and $R^2$ are, same or different, a lower alkyl group, a lower alkenyl group, a lower alkynyl group or a lower alkyl group substituted with at least one member selected from the group consisting of halogen, lower alkoxy and lower cycloalkyl; $R^3$ is a $C_1$-$C_8$ alkyl group, a $C_3$-$C_8$ alkenyl group, a $C_3$-$C_8$ alkynyl group, lower cycloalkyl group, a lower haloalkenyl group, a lower haloalkynyl group, a lower aralkyl group, a lower alkyl group substituted with at least one member selected from the group consisting of halogen, cyano, lower alkoxy, lower alkenyloxy, lower haloalkoxy, phenoxy, lower aralkyloxy and lower cycloalkyl; X and Y are, same or different, an oxygen atom or a sulfur atom; and Z is a hydrogen atom, a lower alkyl group, a lower alkenyl group, a lower alkynyl group, a lower cycloalkyl group, a lower haloalkenyl group, a lower alkyl group substituted with at least one member selected from the group consisting of halogen, cyano, lower alkoxy and lower alkoxycarbonyl, or a group of the formula: —$COR^4$ or —$SO_2R^4$ in which $R^4$ is a lower alkyl group, a lower alkenyl group, a lower alkynyl group, a lower cycloalkyl group, a lower haloalkenyl group, a lower alkyl group substituted with at least one member selected from the group consisting of halogen, cyano, lower alkoxy, lower cycloalkyl and phenoxy (phenoxy being optionally substituted with at least one halogen and/or at least one alkyl), a phenyl group, a furyl group, a phenyl group substituted with at least one member selected from the group consisting of halogen, cyano, nitro, trifluoromethyl, lower alkyl and lower alkoxy, or an aralkyl group (aralkyl being optionally substituted with at least one halogen and/or at least one alkyl), with the proviso that when $R^1$ is methyl, $R^2$ is neither methyl nor butyl, and an inert carrier or diluent.

22. The fungicidal composition according to claim 21, which further comprises as an additional active ingredient(s) a benzimidazole thiophanate fungicide and/or a cyclic imide fungicide.

23. The fungicidal composition according to claim 22, wherein the benzimidazole thiophanate fungicide includes methyl 1-(butylcarbamoyl)benzimidazol-2-ylcarbamate, 2-(2-furyl)benzimidazole, methyl benzimidazol-2-ylcarbamate, and said cyclic imide fungicide includes 3-(3',5'-dichlorophenyl)-1,2-dimethylcyclopropane-1,2-dicarboximide, 3-(3',5'-dichlorophenyl)-1-isopropylcarbamoylimidazolidine-2,4-dione, 3-(3',5'-dichlorophenyl)-5methyl-5-vinyloxazoline-2,4-dione or ethyl(RS)-3-(3',5'-dichlorophenyl)-5-methyl-2,4-dioxooxazolidine-5-carboxylate.

24. An N-phenylcarbamate of the formula:

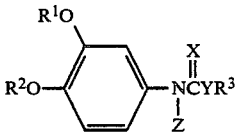

wherein $R^1$ and $R^2$ are, same or different, a lower alkyl group, a lower alkenyl group, a lower alkynyl group or a lower alkyl group substituted with at least one member selected from the group consisting of halogen, lower alkoxy and lower cycloalkyl; $R^3$ is a $C_1$-$C_8$ alkyl group, a $C_3$-$C_8$ alkenyl group, a $C_3$-$C_8$ alkynyl group, lower cycloalkyl group, a lower haloalkenyl group, a lower haloalkynyl group, a lower aralkyl group, a lower alkyl group substituted with at least one member selected from the group consisting of halogen, cyano, lower alkoxy, lower alkenyloxy, lower haloalkoxy, phenoxy, lower aralkyloxy and lower cycloalkyl; X and Y are, same or different, an oxygen atom or a sulfur atom; and Z is a hydrogen atom, a lower alkyl group, a lower alkenyl group, a lower alkynyl group, a lower cycloalkyl group, a lower haloalkenyl group, a lower alkyl group substituted with at least one member selected from the group consisting of halogen, cyano, lower alkoxy and lower alkoxycarbonyl, or a group of the formula: —COR$^4$ or —SO$_2$R$^4$ in which R$^4$ is a lower alkyl group, a lower alkenyl group, a lower alkynyl group, a lower cycloalkyl group, a lower haloalkenyl group, a lower alkyl group substituted with at least one member selected from the group consisting of halogen, cyano, lower alkoxy, lower cycloalkyl and phenoxy (phenoxy being optionally substituted with at least one halogen and/or at least one alkyl), a phenyl group, a furyl group, a phenyl group substituted with at least one member selected from the group consisting of halogen, cyano, nitro, trifluoromethyl, lower alkyl and lower alkoxy, or an aralkyl group (aralkyl being optionally substituted with at least one halogen and/or at least one alkyl), with the proviso that when R$^1$ is methyl, R$^2$ is neither methyl nor butyl.

25. The N-phenylcarbamate according to claim 24, wherein R$^1$ and R$^2$ are independently methyl, ethyl, n-propyl, isopropyl, n-butyl, allyl, 2-butenyl, 3-butenyl, propargyl, 3-butynyl, difluoromethyl, 2-chloroethyl, 2,2,2-trifluoroethyl, 2-methoxyethyl or cyclopropylmethyl, R$^3$ is methyl, ethyl, n-propyl, isopropyl, sec-butyl, 1-ethylpropyl, 1-methylbutyl, 1-ethylbutyl, 2-butenyl, 3-butenyl, 2-methyl-2-propenyl, 1-ethyl-2-propenyl, 1-methyl-3-butenyl, 1-pentyl-2-propenyl, propargyl, 1-methyl-2-propynyl, 2-butynyl, 3-butynyl, 1-ethyl-2-propynyl, 1-methyl-3-butynyl, 1-butyl-2-propynyl, 1-pentyl-2-propynyl, cyclobutyl, cyclopentyl, 2-fluoroethyl, 2-chloroethyl, 2,2-dichloroethyl, 1-methyl-2-bromoethyl, 1-fluoromethyl-2-fluoroethyl, 1-bromomethyl-2bromoethyl, 1-methyl-2,2,2-trichloroethyl, 1-ethyl-2-bromoethyl, 4-chloro-2-butenyl, 4-chloro-2-butynyl, 2-cyanoethyl, 1-methyl-2-methoxyethyl, 1-methyl-2-butoxyethyl, 2-allyloxyethyl, 2-(2-chloroethoxy)ethyl, 2-benzyloxyethyl, 1-chloromethyl-2-methoxyethyl, cyclopropylmethyl, 1-cyclopropylethyl, 1-cyclopentylethyl, 2-furylmethyl, 1-phenylethyl or 3-tetrahydrofuranyl; X and Y are independently oxygen or sulfur; and z is hydrogen, methyl, ethyl, n-butyl, allyl, acetyl, propionyl, n-pentanoyl, sec-pentanoyl, cyclopropanecarbonyl, benzoyl, 2-chlorobenzoyl, 2,4-dichlorobenzoyl, 4-methylbenzoyl, methanesulfonyl or ethoxycarbonylmethyl, with the proviso that when R$^1$ is methyl, R$^2$ is neither methyl nor butyl.

26. The N-phenylcarbamate according to claim 25, wherein R$^1$ and R$^2$ are independently methyl, ethyl, n-propyl, allyl or propargyl, R$^3$ is ethyl, isopropyl, sec-butyl, 1-methylbutyl, 1-ethylpropyl, 1-ethylbutyl, 1-methyl-2-propenyl, 1-ethyl-2-propenyl, 1-methyl-3-butenyl, propargyl, 1-methyl-2-propynyl, 1-ethyl-2-propynyl, 3-butynyl, 1-methyl-3-butynyl, 1-butyl-2-propynyl, 2-fluoroethyl, 1-methyl-2-bromoethyl, 1-fluoromethyl-2-fluoroethyl, 1-bromomethyl-2-bromoethyl, 4-chloro-2-butynyl, 1-methyl-2-methoxyethyl, 1-cyclopropylethyl or 1-phenylethyl; X is oxygen, Y is oxygen or sulfur; and Z is hydrogen, acetyl, propionyl, n-pentanoyl, sec-pentanoyl, cyclopropanecarbonyl, benzoyl, 2-chlorobenzoyl, 2,4-dichlorobenzoyl, or 4-methylbenzoyl, with the proviso that when R$^1$ is methyl, R$^2$ is not methyl.

27. The N-phenylcarbamate according to claim 26, wherein R$^1$ and R$^2$ are ethyl, R$^3$ is ethyl, isopropyl, sec-butyl, 1-methylbutyl, 1-ethylbutyl, 1-methyl-3-butenyl, 1-methyl-2-propynyl, 4-chloro-2-butynyl or 1-phenylethyl, X is oxygen, Y is oxygen or sulfur and Z is hydrogen, acetyl, cyclopropanecarbonyl, benzoyl or 2-chlorobenzoyl.

28. The N-phenylcarbamate according to claim 24, Isopropyl N-(3,4-diethoxyphenyl)carbamate.

29. The N-phenylcarbamate according to claim 24, 1-Methyl-2-propynyl N-(3,4-diethoxyphenyl)carbamate.

30. The N-phenylcarbamate according to claim 24, 4-Chloro-2-butynyl N-(3,4-diethoxyphenyl)carbamate.

31. The N-phenylcarbamate according to claim 24, Isopropyl N-(3,4-diethoxyphenyl)thiolcarbamate.

32. The N-phenylcarbamate according to claim 24, 1-Phenylethyl N-(3,4-diethoxyphenyl)carbamate.

33. The N-phenylcarbamate according to claim 24, Isopropyl N-acetyl-N-(3,4-diethoxyphenyl)carbamate.

34. The N-phenylcarbamate according to claim 24, Isopropyl N-cyclopropanecarbonyl-N-(3,4-diethoxyphenyl)carbamate.

35. The N-phenylcarbamate according to claim 24, Isopropyl N-benzony-N-(3,4-diethoxyphenyl)carbamate.

36. The N-phenylcarbamate according to claim 24, Isopropyl N-(2-chlorobenzoyl)-N-(3,4-diethoxyphenyl)carbamate.

37. A method for controlling plant pathogenic fungi which comprises applying a fungicidally effective amount of at least one of the N-phenylcarbamates of the formula:

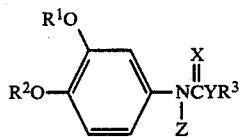

wherein R$^1$, R$^2$, R$^3$, X, Y and Z are each as defined in claim 21, to plant pathogenic fungi.

38. The method according to claim 37, wherein the plant pathogenic fungi is the drug-resistant strain.

39. A method for controlling plant pathogenic fungi which comprises applying a fungicidally effective amount of a mixture of the N-phenylcarbamate of the formula:

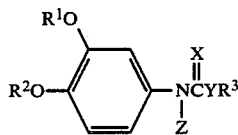

wherein R$^1$ R$^2$, R$^3$, X, Y and Z are each as defined in claim 21, and a benzimidazole thiophanate fungicide and/or a cyclic imide fungicide.

40. The n-phenylcarbamate according to claim 24, ethyl N-(3,4-diethoxyphenyl)carbamate.

41. A fungicidal composition according to claim 21, wherein said n-phenylcarbamate is ethyl N-(3,4-diethoxyphenyl)carbamate.

42. A method for controlling plant pathogenic fungi according to claim 37, wherein said n-phenylcarbamate is ethyl N-(3,4-diethoxyphenyl)carbamate.

* * * * *